US007863247B1

(12) United States Patent
Brenneman et al.

(10) Patent No.: US 7,863,247 B1
(45) Date of Patent: *Jan. 4, 2011

(54) PREVENTION OF FETAL ALCOHOL SYNDROME AND NEURONAL CELL DEATH WITH ADNF POLYPEPTIDES

(75) Inventors: Douglas E. Brenneman, Damascus, MD (US); Catherine Y. Spong, Arlington, VA (US); Illana Gozes, Ramat Hasharon (IL); Merav Bassan, Hod Hasharon (IL); Rachel Zamostiano, Hod Hasharon (IL)

(73) Assignee: Ramot-University Authority for Applied Research and Development Ltd., Tel-Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/936,888

(22) PCT Filed: Mar. 10, 2000

(86) PCT No.: PCT/US00/06364

§ 371 (c)(1),
(2), (4) Date: Sep. 3, 2002

(87) PCT Pub. No.: WO00/53217

PCT Pub. Date: Sep. 14, 2000

(51) Int. Cl.
*A61K 38/00* (2006.01)
*A61K 39/00* (2006.01)
*A61K 38/24* (2006.01)
*A01N 37/18* (2006.01)
*C07K 1/00* (2006.01)

(52) U.S. Cl. .................. 514/14; 514/12; 424/184.1; 424/185.1; 424/198.1; 530/350; 530/399

(58) Field of Classification Search .............. None
See application file for complete search history.

(56) References Cited

U.S. PATENT DOCUMENTS

| 5,767,240 | A  | 6/1998  | Brenneman et al. |
| 6,174,862 | B1 | 1/2001  | Brenneman |
| 6,613,740 | B1 | 9/2003  | Gozes et al. |
| 6,649,411 | B2 | 11/2003 | Gozes et al. |
| 7,264,947 | B2 | 9/2007  | Gozes et al. |
| 7,452,867 | B2 | 11/2008 | Gozes et al. |
| 2004/0235747 | A1 | 11/2004 | Gozes et al. |
| 2007/0054847 | A1 | 3/2007  | Gozes et al. |
| 2009/0124543 | A1 | 5/2009  | Gozes et al. |
| 2009/0137469 | A1 | 5/2009  | Gozes et al. |
| 2009/0170780 | A1 | 7/2009  | Gozes et al. |

FOREIGN PATENT DOCUMENTS

| WO | WO 92/18140 A1 | 10/1992 |
| WO | WO 96/11948 A1 | 4/1996 |
| WO | WO 98/35042 A1 | 8/1998 |
| WO | WO 00/53217 A2 | 9/2000 |

OTHER PUBLICATIONS

Roth et al., 1999, Ann. Rev. Biomed. Eng., 01, pp. 265-297.*
Welsh, 1999, Current Opinion in Mol. Therapeutics, 1 (4), pp. 464-470.*
Bassan, M. et al. "Complete Sequence of a Novel ProteinContaining a Femtomolar-Activity-Dependent Neuroprotective Peptide." *Journal of Neurochemistry* 72:1283-1293 (1999).
Bassan, M. et al. "VIP-Induced Mechanism of Neuroprotection: The Complete Sequence of a Femtomolar-Acting Activity-Dependent Neuroprotective Protein." *Regulatory Peptides*, 71(2): , Aug. 15, 1997.
Beni-Adani, L. et al. "Activity-Dependent Neurotrophic Protein is Neuroprotective in a Mouse Model of Closed Head Injury." Society for Neuroscience, 28th Annual Meeting, Los Angeles, CA, Nov. 7-12, 1998. *Abstracts* 23(1):1043 (1998).
Brenneman et al. "Neuronal Cell Killing by the Envelope Protein of HIV and Its Prevention by Vasoactive Intestinal Peptide." *Nature* 335:636 (1988).
Brenneman et al. "*N*-Methyl-D-Aspartate Receptors Influence Neuronal Survival in Developing Spinal Cord Cultures" *Dev. Brain Res.* 51:63 (1990).
Brenneman, D.C. and Gozes, I. "A Femtomolar-Acting Neuroprotective Peptide." *Journal of Clinical Investigation* 97:229-230 (1996).
Brenneman, D.E. et al. "Activity-Dependent neutotrophic Factor: Structure-Activity Relationships of Femtomolar-Acting Peptides." *Journal of Pharmacology and Experimental Therapeutics* 285: 619-627 (1998).
Brenneman, D.E. et al. "Identification of a Nine Amino Acid Core Peptide from Activity Dependent Neurotrophic Factor I." Society for Neuroscience, 27th Annual Meeting, New Orleans, LA, Oct. 25-30, 1997. *Abstracts* 23(2): 2250 (1997).
Davidson, A. et al. "Protection Against Developmental Retardation and Learning Impairments in Apolipoprotein E-Deficient Mice by Activity-Dependent Femtomolar-Acting Peptides." Society for Neuroscience, 27th Annual Meeting, New Orleans, LA, Oct. 25-30, 1997. *Abstracts* 23(2)2250 (1997).

(Continued)

*Primary Examiner*—Olga N Chernyshev
(74) *Attorney, Agent, or Firm*—Townsend and Townsend and Crew LLP

(57) ABSTRACT

The invention relates to methods for reducing a condition associated with fetal alcohol syndrome in a subject who is exposed to alcohol in utero with an ADNF polypeptide (e.g, ADNF I polypeptides, ADNF III polypeptides, or mixtures of ADNF I and ADNF III polypeptides). In one embodiment, the present invention relates to methods for reducing a condition associated with fetal alcohol syndrome in a subject who is exposed to alcohol in utero with a mixture of ADNF I and ADNF III polypeptides. The present invention further relates to methods for reducing neuronal cell death by contacting neuronal cells with a mixture of ADNF I and ADNF III polypeptides. Still further, the present invention relates to a pharmaceutical composition comprising a mixture of ADNF I and ADNF III polypeptides.

21 Claims, 6 Drawing Sheets

OTHER PUBLICATIONS

Dibbern, D.A., Jr. et al. "Inhibition of Murine Embryonic Growth by Human Immunodeficiency Virus Envelope Protein and Its Prevention by Vasoactive Intestinal Peptide and Activity-Dependent Neurotrophic Factor." *Journal of Clinical Investigation* 99: 2837-2841 (1997).

Giladi, E. "Protection Against Developmental and Learning Impairments in Apolipoprotein E-Deficient Mice by Activity-Dependent Femtomolar-Acting Peptides." *Neuroscience Letters* Supplement 48 S1-S60, p. S19 (1997).

Glazner, G.W. et al. "A 9 Amino Acid Peptide Fragment of Activity-Dependent Neurotrophic Factor (ADNF) Protects Neurons from Oxidative Stress-Induced Death." Society for Neuroscience, $27^{th}$ Annual Meeting, New Orleans, LA, Oct. 25-30, 1997. *Abstracts* 23(2)2249 (1997).

Glazner, G.W. et al. "Activity Dependent Neurotrophic Factor: A Potent Regulator of Embryonic Growth." *Anat. Embryol.* 200:65-71 (1999).

Gozes I. et al. "Antiserum to Activity-Dependent Neurotrophic Factor Produces Neuronal Cell Death in CNS Cultures: Immunological and Biological Specificity." *Developmental Brain Research* 99:167-175 (1997).

Gozes, I. and Brenneman, D.E. "Activity-Dependent Neurotrophic Factor (ADNF)." *Journal of Molecular Neuroscience* 7:235-244 (1996).

Gozes, I. et al. A Femtomolar-Acting Activity-Dependent Neuroprotective Protein (ADNP). *Neuroscience Letters* Supplement 48 S1-S60, p. S21 (1997)-.

Gozes, I. et al. "Protection Against Developmental Retardation in Apolipoprotein E-Deficient Mice by a Fatty neuropeptide: Implications for Early Treatment of Alzheimer's Disease." *Journal of Neurobiology* 33:329-342 (1997).

Gozes, I. et al. "Stearyl-Norleucine-Vasoactive Intestinal Peptide (VIP): A Novel VIP Analog for Noninvasive Impotence Treatment." *Endocrinology* 134: 2125 (1994).

Gozes, I. et al. "Superactive Lipophilic Peptides Discriminate Multiple Vasoactive intestinal Peptide Receptors." *Journal of Pharmacology and Experimental Therapeutics* 27:3161-167 (1995).

Gozes, I. et al. "The cDNA Structure of a Novel Femtomolar-Acting Neuroprotective Protein: Activity-Dependent-Neurotrophic Factor III (ADNFIII)." Society for Neuroscience, $27^{th}$ Annual Meeting, New Orleans, LA, Oct. 25-30, 1997. *Abstracts* 23(2):2250 (1997).

Gozes, I. et al. "Neuroprotective Strategy for Alzheimer Disease: Intranasal Administration of a Fatty Neuropeptide." *Proc. Natl. Acad. Sci. USA* 93:427-432 (1996).

Gressens, P. et al. "Growth Factor Function of Vasoactive Intestinal Peptide in Whole Cultured Mouse Embryos." *Nature* 362:155-58 (1993).

Hannigan, J.H. and Berman, R.F. "Amelioration of Fetal Alcohol-Related Neurodevelopmental Disorders in Rats: Exploring Pharmacological and Environmental Treatments." *Neurotoxicol. & Teratol.* 22(1):103-111 (2000).

Hill, J.M. et al. "Learning Impairment in Adult Mice Produced by Early Embryonic Administration of Antiseum to Activity-Dependent Neurotrophic Factor (ADNF)." Society for Neuroscience, $27^{th}$ Annual Meeting, New Orleans, LA, Oct. 25-30, 1997. *Abstracts* 23(2):2250 (1997).

Lilling, G. et al. "Inhibition of Human Neuroblastoma Growth by a Specific VIP Antagonist." *Journal of Molecular Neuroscience* 5: 231-239 (1995).

Mahato et al. "Development of Targeted Delivery Systems for Nucleic Acid Drugs." *J. of Drug Targeting* 4(6):337-357 (1997).

McKune, S.K. et al. "Localization of mRNA for Activity-Dependent Neurotrophic Factor III (ADNF III) in mouse Embryo and Adult CNS." Society for Neuroscience, $27^{th}$ Annual Meeting, New Orleans, LA, Oct. 25-30, 1997. *Abstracts* 23(2):2249 (1997).

Nelbock, P. et al. A cDNA for a Protein that Interacts with the Human Immunodeficiency Virus Tat Transactivator. *Science*, 248:1650-1653 (1990).

Oberdoester, J. et al. "The Effects of Ethanol on Neuronal Cell Death: Implication for the Fetal Alcohol Syndrome." *FASEB Journal* 12(4):A134 (Mar. 17, 1998).

Pelsman, A. et al. "In Vitro Degeneration of Down Syndrome neurons is Prevented by Activity-Dependent Neurotrophic Factor-Derived Peptides." Society for Neuroscience, $28^{TH}$ Annual Meeting, Los Angeles, CA, Nov. 7-12, 1998. *Abstracts* 24:1044 (1998).

Skolnick, J. and Fetrow, J.S. "Form Genes to Protein Structure and Function: Novel Applications of Computational Approaches in the Genomic Era." *Trends in Biotech.* 18(1):34-39 (2000).

Smith, A.E. "Viral Vectors in Gene Therapy." *Ann. Rev.Microbiol.* 49:807-838 (1995).

Spinney, L. "New Peptides Prevent Brain Damage." *Molecular Medicine Today* 5(7):282 (Jul. 1999).

Spong et al. "Prevention of Fetal Alcohol Syndrome by Novel Peptides." *FASEB Journal* 13(5):A881.

Gozes, I., et al., U.S. Appl. No. 12/708,384, filed Feb. 18, 2010, titled "Neuroprotection Using Nap-Like and Sal-Like Peptide Mimetics," 57 pgs.

* cited by examiner

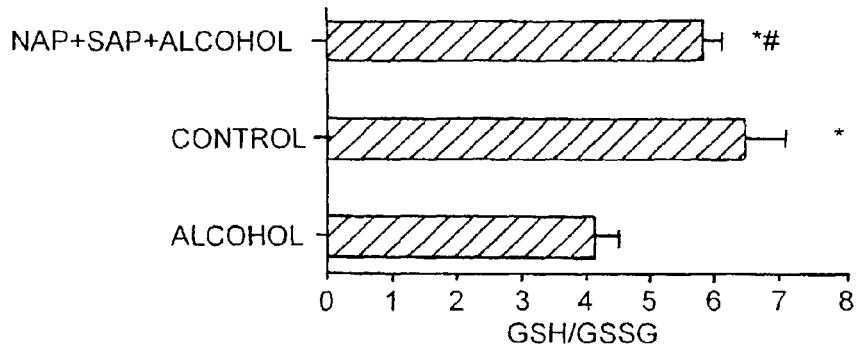

\* = SIGNIFICANTLY DIFFERENT VS ALCOHOL
\# = NOT SIGNIFICANTLY DIFFERENT VS CONTROL

ANOVA TABLE FOR GSH TO GSSG

|  | DF | SUM OF SQUARES | MEAN SQUARE | F-VALUE | P-VALUE |
|---|---|---|---|---|---|
| GROUP | 2 | 27.517 | 13.758 | 6.892 | .0047 |
| RESIDUAL | 22 | 43.917 | 1.996 |  |  |

MODEL II ESTIMATE OF BETWEEN COMPONENT VARIANCE: 1.414
7 CASES WERE OMITTED DUE TO MISSING VALUES.

MEAN TABLE FOR GSH TO GSSG
EFFECT: GROUP

|  | COUNT | MEAN | STD. DEV. | STD. ERR. |
|---|---|---|---|---|
| ALCOHOL | 9 | 4.067 | 1.125 | .375 |
| CONTROL | 8 | 6.532 | 1.938 | .685 |
| NAP+SAL+ALCOHOL | 8 | 5.798 | 1.034 | .366 |

7 CASES WERE OMITTED DUE TO MISSING VALUES.

FIG. 6.

PREVENTION OF FETAL ALCOHOL SYNDROME AND NEURONAL CELL DEATH WITH ADNF POLYPEPTIDES

CROSS-REFERENCES TO RELATED APPLICATIONS

This application claims priority to application U.S. Ser. No. 09/267,511, filed Mar. 12, 1999, the disclosure of which is herein incorporated by reference in its entirety. This application is also related to U.S. Ser. No. 07/871,973 filed Apr. 22, 1992, now U.S. Pat. No. 5,767,240, issued Jun. 16, 1998; U.S. Ser. No. 08/342,297, filed Oct. 17, 1994 (published as WO96/11948); U.S. Ser. No. 60/037,404, filed Feb. 27, 1997 (published as WO98/35042); and U.S. Ser. No. 09/187,330, filed Nov. 11, 1998. All of these applications are incorporated herein by reference.

STATEMENT AS TO RIGHTS TO INVENTIONS MADE UNDER FEDERALLY SPONSORED RESEARCH AND DEVELOPMENT

Not applicable.

FIELD OF THE INVENTION

This invention relates to methods for reducing a condition associated with fetal alcohol syndrome in a subject who is exposed to alcohol in utero with an ADNF polypeptide (e.g., ADNF I polypeptides, ADNF III polypeptides, mixtures of ADNF I and ADNF III polypeptides). The present invention further relates to methods for reducing neuronal cell death by contacting neuronal cells with a mixture of ADNF I and ADNF III polypeptides. Still further, the present invention relates to a pharmaceutical composition comprising a mixture of ADNF I and ADNF III polypeptides.

BACKGROUND OF THE INVENTION

In the United States, fetal alcohol syndrome (FAS) affects 12,000 babies each year and the rate of frequent drinking during pregnancy has increased four-fold between 1991 and 1995 (*MMWR* 46:346-50 (1997)). Maternal alcohol consumption is the most commonly identifiable non-genetic cause of mental retardation. In addition, consuming over 3 drinks per week in the first trimester has been shown to double the risk of miscarriage (Windham et al., *Epidemiology* 8:509-14 (1997)). An increase in free radical formation has been implicated in the pathogenesis of alcohol-induced central nervous system dysfunction in FAS. Ethanol treatment in cell culture depresses cell viability and generates reactive oxygen intermediates including superoxide, hydrogen peroxide and hydroxyl anions (Guerri et al., *Free Radicals in Diagnostic Medicine*, Plenum Press, New York, 291-305 (1994)). Acute alcohol exposure has been shown to increase superoxide generation and decrease extraperoxisomal catalase activity, decreasing Cu, Zn-superoxide dismutase activity (Nordmann et al., *Free Radical Biology and Medicine* 12:219-40 (1992)).

The most devastating effects of alcohol exposure occur during organogenesis and development of the nervous system (Armant et al., *Sem. Perinatol.*, 20:127-39 (1996)), during the time when vasoactive intestinal peptide (VIP) has been shown to regulate mouse embryonic growth (Gressens et al., *Nature*, 362:155-8 (1993)). There are known interactions between alcohol and VIP, a neuropeptide that is a regulator of early postimplantation mouse embryonic growth (Gressens et al., *J. Clin. Invest.* 94:2020-2027 (1994)). In pregnant mice, both alcohol and VIP antagonist treatment may result in some of the features of FAS, including fetal growth restriction and microcephaly. Interactions between alcohol and VIP include a decrease in VIP mRNA in the suprachiasmatic nucleus with alcohol exposure (Maderia et al., *J. Neurosci.* 17:1302-19 (1997)), and a decrease in VIP binding in rat enterocytes after chronic alcohol consumption (Jimenez et al., *Gen. Pharmac.* 23:607-11 (1992)). Ethanol has also been shown to result in cell death in the neuroepithelium (Gressens et al., *Alc. & Alc.* 27:219-26 (1992)), which is a prominent site of VIP binding (Hill et al., *J. Comp. Neurol.* 342:186-205 (1994)).

Individuals who were exposed to alcohol in utero may suffer from various mental and physical defects associated with fetal alcohol syndrome. For example, they may suffer from growth retardations; physical, mental, and behavioral abnormalities; central nervous system impairment, including developmental delay, small head size, and speech or language delay; and facial abnormalities.

In view of its severe and lifelong impact on the fetus, fetal alcohol syndrome is a major public concern. Although educating the public, in particular pregnant women, regarding consumption of alcohol and its effect on the fetus and refraining from drinking during pregnancy are the obvious, sensible approach to resolving this problem, this approach alone has not been effective as illustrated by the alarming statistics set forth above. Another method which can be used in conjunction with educating the public is approaching this problem clinically, i.e., intervening against alcohol induced damages by treating pregnant women and unborn fetus with prophylactic compounds. Therefore, there is a need to identify and isolate compounds which can reduce fetal alcohol syndrome. The identification and isolation of new compounds would allow aid in the reduction and prevention of fetal alcohol syndrome and other related medical conditions. The present invention meets this and other needs.

SUMMARY OF THE INVENTION

The present invention provides for the first time methods for reducing a condition associated with fetal alcohol syndrome in a subject who is exposed to alcohol in utero using ADNF polypeptides. The present invention further provides methods for reducing neuronal cell death using a mixture of ADNF I and ADNF III polypeptides. Still further, the present invention provides a pharmaceutical composition comprising a mixture of ADNF I and ADNF III polypeptides.

The ADNF polypeptides include ADNF I and ADNF III polypeptides and subsequences thereof which contain their respective active core sites and provide neuroprotective and growth-promoting functions. The ADNF I polypeptides have an active core site comprising the following amino acid sequence: Ser-Ala-Leu-Leu-Arg-Ser-Ile-Pro-Ala ("SALLR-SIPA" or in short referred to as "SAL"; SEQ ID NO:1). The ADNF III polypeptides also have an active core site comprising a few amino acid residues, namely, the following amino acid sequence: Asn-Ala-Pro-Val-Ser-Ile-Pro-Gln ("NAPV-SIPQ" or in short referred as "NAP"; SEQ ID NO:2). These ADNF polypeptides have previously been shown, each on their own, to have remarkable potency and activity in animal models related to neurodegeneration. However, ADNF polypeptides have not previously been shown to reduce or prevent a condition associated with fetal alcohol syndrome. The effects of ADNF polypeptides on a condition associated with fetal alcohol syndrome are demonstrated for the first time in this application.

As such, in one aspect, the present invention provides a method for reducing a condition associated with fetal alcohol syndrome in a subject who is exposed to alcohol in utero, the method comprising administering to the subject an ADNF polypeptide in an amount sufficient to reduce the condition associated with fetal alcohol syndrome. Such conditions include, for example, decreased learning, decreased body weight, decreased brain weight, decreased VIP mRNA or protein, and decreased viability of the subject in utero, decreased glutathione level, etc.

In one embodiment, the method comprises administering an ADNF polypeptide, wherein the ADNF polypeptide is an ADNF I polypeptide comprising an active core site having the amino acid sequence of Ser-Ala-Leu-Leu-Arg-Ser-Ile-Pro-Ala (SEQ ID NO:1). In another embodiment, the method comprises administering a full length ADNF I polypeptide. In yet another embodiment, the method comprises administering an ADNF I polypeptide which consists of the amino acid sequence of Ser-Ala-Leu-Leu-Arg-Ser-Ile-Pro-Ala (SEQ ID NO:1). In yet another embodiment, the method comprises administering an ADNF I polypeptide, wherein the ADNF I polypeptide is selected from the group consisting of: Val-Leu-Gly-Gly-Gly-Ser-Ala-Leu-Leu-Arg-Ser-Ile-Pro-Ala (SEQ ID NO:14); Val-Glu-Glu-Gly-Ile-Val-Leu-Gly-Gly-Gly-Ser-Ala-Leu-Leu-Arg-Ser-Ile-Pro-Ala (SEQ ID NO:15); Leu-Gly-Gly-Gly-Ser-Ala-Leu-Leu-Arg-Ser-Ile-Pro-Ala (SEQ ID NO:16); Gly-Gly-Gly-Ser-Ala-Leu-Leu-Arg-Ser-Ile-Pro-Ala (SEQ ID NO:17); Gly-Gly-Ser-Ala-Leu-Leu-Arg-Ser-Ile-Pro-Ala (SEQ ID NO:18); and Gly-Ser-Ala-Leu-Leu-Arg-Ser-Ile-Pro-Ala (SEQ ID NO:19). In yet another embodiment, the method comprises administering an ADNF I polypeptide having up to about 20 amino acids at least one of the N-terminus or the C-terminus of the active core site. In certain embodiments, the ADNF I polypeptide has up to 20 amino acids at both the N-terminus and the C-terminus of the ADNF I polypeptide.

In another embodiment, the method comprises administering an ADNF polypeptide, wherein the ADNF polypeptide is an ADNF III polypeptide comprising an active core site having the amino acid sequence of Asn-Ala-Pro-Val-Ser-Ile-Pro-Gln (SEQ ID NO:2). In yet another embodiment, the method comprises administering a full length ADNF III polypeptide. In yet another embodiment, the method comprises administering an ADNF I polypeptide which consists of the amino acid sequence of Asn-Ala-Pro-Val-Ser-Ile-Pro-Gln (SEQ ID NO:2). In yet another embodiment, the method comprises administering an ADNF III polypeptide, wherein the ADNF III polypeptide is selected from the group consisting of: Gly-Gly-Asn-Ala-Pro-Val-Ser-Ile-Pro-Gln (SEQ ID NO:20); Leu-Gly-Gly-Asn-Ala-Pro-Val-Ser-Ile-Pro-Gln-Gln-Ser (SEQ ID NO:21); Leu-Gly-Leu-Gly-Gly-Asn-Ala-Pro-Val-Ser-Ile-Pro-Gln-Gln-Ser (SEQ ID NO:22); and Ser-Val-Arg-Leu-Gly-Leu-Gly-Gly-Asn-Ala-Pro-Val-Ser-Ile-Pro-Gln-Gln-Ser (SEQ ID NO:23). In yet another embodiment, the method comprises administering an ADNF III polypeptide having up to about 20 amino acids at least one of the N-terminus and the C-terminus of the active core site. In certain embodiments, the ADNF III polypeptide has up to 20 amino acids at both the N-terminus and the C-terminus of the ADNF III polypeptide.

In yet another embodiment, the method comprises administering a mixture of an ADNF I polypeptide and an ADNF III polypeptide. Any one or more of the ADNF I polypeptides described herein can be mixed with any one or more of the ADNF III polypeptides described herein in this and other aspects of the invention.

In yet another embodiment, at least one of the ADNF polypeptide is encoded by a nucleic acid which is administered to the subject.

In yet another embodiment, the condition associated with fetal alcohol syndrome in a subject is decreased body weight of the subject. In yet another embodiment, the condition associated with fetal alcohol syndrome in a subject is decreased brain weight of the subject. In yet another embodiment, the condition associated with fetal alcohol syndrome in a subject is decreased level of VIP mRNA or protein of the subject. In yet another embodiment, the condition associated with fetal alcohol syndrome in a subject is decreased viability of the subject in utero. In yet another aspect, the condition associated with fetal alcohol syndrome in a subject is decreased learning or learning deficits.

In another aspect, the present invention provides a method for reducing neuronal cell death, the method comprising contacting a neuronal cell with a mixture of an ADNF I polypeptide and an ADNF III polypeptide in an amount sufficient to reduce neuronal cell death.

In one embodiment, the ADNF polypeptide used to reduce neuronal cell death is a mixture of an ADNF I polypeptide that comprises an active core site having the amino acid sequence of Ser-Ala-Leu-Leu-Arg-Ser-Ile-Pro-Ala (SEQ ID NO:1) and an ADNF III polypeptide that comprises an active core site having the amino acid sequence of Asn-Ala-Pro-Val-Ser-Ile-Pro-Gln (SEQ ID NO:2). In another embodiment, the ADNF polypeptide used in the method is a mixture of a full length ADNF I polypeptide and a full length ADNF III polypeptide. In yet another embodiment, the ADNF polypeptide used in the method is a mixture of an ADNF I polypeptide which consists of the active core site having the amino acid sequence of Ser-Ala-Leu-Leu-Arg-Ser-Ile-Pro-Ala (SEQ ID NO:1) and an ADNF III polypeptide which consists of the active core site having the amino acid sequence of Asn-Ala-Pro-Val-Ser-Ile-Pro-Gln (SEQ ID NO:2). In yet another embodiment, the ADNF polypeptide mixture comprises an ADNF I polypeptide which is selected from the group consisting of: Val-Leu-Gly-Gly-Gly-Ser-Ala-Leu-Leu-Arg-Ser-Ile-Pro-Ala (SEQ ID NO:14); Val-Glu-Glu-Gly-Ile-Val-Leu-Gly-Gly-Gly-Ser-Ala-Leu-Leu-Arg-Ser-Ile-Pro-Ala (SEQ ID NO:15); Leu-Gly-Gly-Gly-Ser-Ala-Leu-Leu-Arg-Ser-Ile-Pro-Ala (SEQ ID NO:16); Gly-Gly-Gly-Ser-Ala-Leu-Leu-Arg-Ser-Ile-Pro-Ala (SEQ ID NO:17); Gly-Gly-Ser-Ala-Leu-Leu-Arg-Ser-Ile-Pro-Ala (SEQ ID NO:18); and Gly-Ser-Ala-Leu-Leu-Arg-Ser-Ile-Pro-Ala (SEQ ID NO:19); and an ADNF III polypeptide which is selected from the group consisting of: Gly-Gly-Asn-Ala-Pro-Val-Ser-Ile-Pro-Gln (SEQ ID NO:20); Leu-Gly-Gly-Asn-Ala-Pro-Val-Ser-Ile-Pro-Gln-Gln-Ser (SEQ ID NO:21); Leu-Gly-Leu-Gly-Gly-Asn-Ala-Pro-Val-Ser-Ile-Pro-Gln-Gln-Ser (SEQ ID NO:22); and Ser-Val-Arg-Leu-Gly-Leu-Gly-Gly-Asn-Ala-Pro-Val-Ser-Ile-Pro-Gln-Gln-Ser (SEQ ID NO:23). In yet another embodiment, the method comprises administering an ADNF I polypeptide and/or an ADNF III polypeptide having up to about 20 amino acids at least one of the N-terminus and the C-terminus of the active core site. In certain embodiments, the ADNF I polypeptide and/or the ADNF III polypeptide has up to 20 amino acids at both the N-terminus and the C-terminus of the polypeptides.

In another aspect, the present invention provides a pharmaceutical composition comprising a pharmaceutically acceptable excipient and a mixture of an ADNF polypeptide and an ADNF III polypeptide.

In one embodiment, the present invention provides a pharmaceutical composition, the pharmaceutical composition comprising a mixture of an ADNF I polypeptide that comprises an active core site having the amino acid sequence of Ser-Ala-Leu-Leu-Arg-Ser-Ile-Pro-Ala (SEQ ID NO:1) and an ADNF III polypeptide that comprises an active core site having the amino acid sequence of Asn-Ala-Pro-Val-Ser-Ile-Pro-Gln (SEQ ID NO:2). In another embodiment, the pharmaceutical composition comprises a mixture of a full length ADNF I polypeptide and a full length ADNF III polypeptide. In yet another embodiment, the pharmaceutical composition comprises a mixture of an ADNF I polypeptide which consists of the active core site having the amino acid sequence of Ser-Ala-Leu-Leu-Arg-Ser-Ile-Pro-Ala (SEQ ID NO:1) and an ADNF III polypeptide which consists of the active core site having the amino acid sequence of Asn-Ala-Pro-Val-Ser-Ile-Pro-Gln (SEQ ID NO:2). In yet another embodiment, the pharmaceutical composition comprises an ADNF I polypeptide which is selected from the group consisting of: Val-Leu-Gly-Gly-Gly-Ser-Ala-Leu-Leu-Arg-Ser-Ile-Pro-Ala (SEQ ID NO:14); Val-Glu-Glu-Gly-Ile-Val-Leu-Gly-Gly-Gly-Ser-Ala-Leu-Leu-Arg-Ser-Ile-Pro-Ala (SEQ ID NO:15); Leu-Gly-Gly-Gly-Ser-Ala-Leu-Leu-Arg-Ser-Ile-Pro-Ala (SEQ ID NO:16); Gly-Gly-Gly-Ser-Ala-Leu-Leu-Arg-Ser-Ile-Pro-Ala (SEQ ID NO:17); Gly-Gly-Ser-Ala-Leu-Leu-Arg-Ser-Ile-Pro-Ala (SEQ ID NO:18); and Gly-Ser-Ala-Leu-Leu-Arg-Ser-Ile-Pro-Ala (SEQ ID NO:19); and an ADNF III polypeptide which is selected from the group consisting of: Gly-Gly-Asn-Ala-Pro-Val-Ser-Ile-Pro-Gln (SEQ ID NO:20); Leu-Gly-Gly-Asn-Ala-Pro-Val-Ser-Ile-Pro-Gln-Gln-Ser (SEQ ID NO:21); Leu-Gly-Leu-Gly-Gly-Asn-Ala-Pro-Val-Ser-Ile-Pro-Gln-Gln-Ser (SEQ ID NO:22); and Ser-Val-Arg-Leu-Gly-Leu-Gly-Gly-Asn-Ala-Pro-Val-Ser-Ile-Pro-Gln-Gln-Ser (SEQ ID NO:23). In yet another embodiment, the pharmaceutical composition comprises an ADNF I polypeptide and/or an ADNF III polypeptide having up to about 20 amino acids at least one of the N-terminus and the C-terminus of the active core site. In certain embodiments, an ADNF I polypeptide and/or an ADNF III polypeptide has up to about 20 amino acids at both the N-terminus and the C-terminus of the polypeptides.

BRIEF DESCRIPTION OF THE DRAWINGS

FIG. 6 illustrates the effects of ADNF polypeptides on glutathione levels. The glutathione levels (both reduced, GSH, and oxidized, GSSG) were measured in gestations (embryo+decidua) 8 h after treatment. Treatment with NAP+SAL significantly prevented alcohol induced decline in GSH/GSSG.

FIG. 7a illustrates a pooled sample of three embryos (different litters) after a thirty minute exposure to $^3$H-NAP. Based on this accumulation of labeled peptide, approximately 1 pmoles of NAP was found in the embryo, with an estimated concentration of 10 nM, well within the therapeutic range of NAP. FIG. 7b illustrates a pooled sample of three embryos (different litters) after a sixty minute exposure to $^3$H-NAP.

Figure 1:
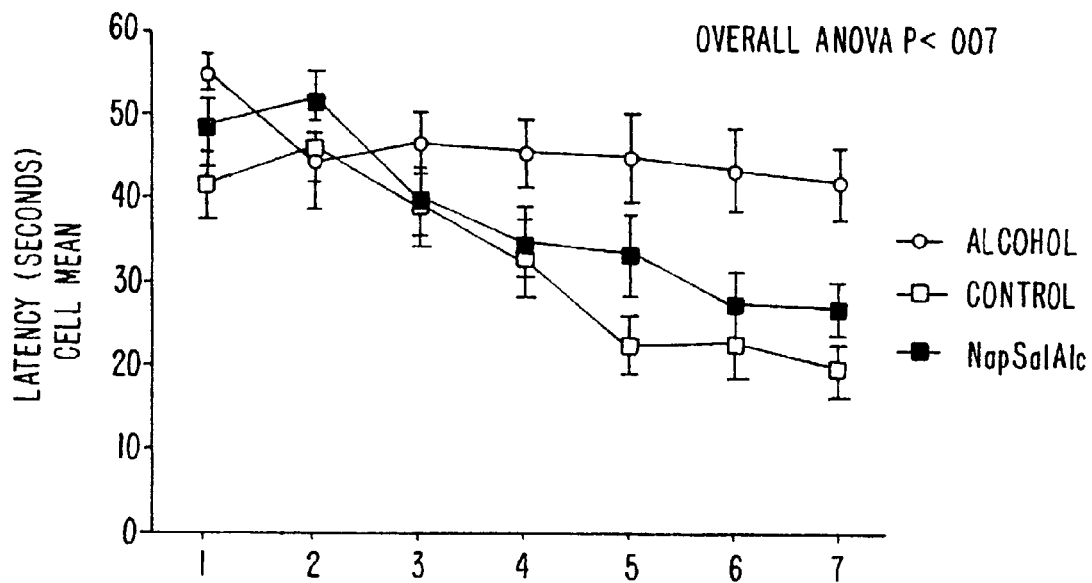
FIG. 1 illustrates that pretreatment with NAP+SAL prevented alcohol-induced learning deficits. Male offspring from litters treated with alcohol (n=9), vehicle (control, n=15), and pre-treatment with NAP+SAL and alcohol (n=15) were tested for latency to find a hidden platform in the Morris Watermaze twice daily for 7 days. Testing began when the males were at least 35 and not more than 50 days of age. Offspring from the alcohol litters did not learn in this paradigm with a latency on day 7 similar to days 1-3. Offspring from the other two groups did significantly learn (decreased latency) over the trials (P<0.001).

In all the figure legends, a peptide having an amino acid sequence of SALLRSIPA (SEQ ID NO:1) is referred to as "SAL," and a peptide having a sequence of NAPVSIPQ (SEQ ID NO:2) is referred to as "NAP."

DEFINITIONS

The phrase "ADNF polypeptide" refers to one or more activity dependent neurotrophic factors (ADNF) that have an active core site comprising the amino acid sequence of SALLRSIPA (SEQ ID NO:1) (referred to as "SAL") or NAPVSIPQ (SEQ ID NO:2) (referred to as "NAP"), or conservatively modified variants thereof that have neurotrophic/neuroprotective activity as measured with in vitro cortical neuron culture assays described by, e.g., Hill et al., *Brain Res.* 603, 222-233 (1993); Venner & Gupta, *Nucleic Acid Res.* 18, 5309 (1990); and Peralta et al., *Nucleic Acid Res.* 18, 7162 (1990); Brenneman et al., *Nature* 335, 636 (1988); or Brenneman et al., *Dev. Brain Res.* 51:63 (1990); Forsythe & Westbrook, *J. Physiol. Lond.* 396:515 (1988). An ADNF polypeptide can be an ADNF I polypeptide, an ADNF III polypeptide, their alleles, polymorphic variants, or interspecies homolog, or any subsequences thereof (e.g., SALLRSIPA (SEQ ID NO:1) or NAPVSIPQ (SEQ ID NO:2)) that exhibit neuroprotective/neurotrophic action on, e.g., neurons originating in the central nervous system either in vitro or in vivo. An "ADNF polypeptide" can also refer to a mixture of an ADNF I polypeptide and an ADNF III polypeptide.

The term "ADNF I" refers to an activity dependent neurotrophic factor polypeptide having a molecular weight of about 14,000 Daltons with a pI of 8.3±0.25. As described above, ADNF I polypeptides have an active site comprising an amino acid sequence of Ser-Ala-Leu-Leu-Arg-Ser-Ile-Pro-Ala (also referred to as "SALLRSIPA" or "SAL"; SEQ ID NO:1). See, Brenneman et al., *J. Clin. Invest.*, 97:2299-2307 (1996), Glazner et al., *Anat Embryol* (In press), Brenneman et al., *J. Pharm. Exp. Ther.*, 285:619-27 (1998), Gozes & Brenneman, *J. Mol. Neurosci.* 7:235-244 (1996), and Gozes et al., *Dev. Brain Res.* 99:167-175 (1997), all of which are herein incorporated by reference. Unless indicated as otherwise, "SAL" refers to a peptide having an amino acid sequence of Ser-Ala-Leu-Leu-Arg-Ser-Ile-Pro-Ala (SEQ ID NO:1), not a peptide having an amino acid sequence of Ser-Ala-Leu.

The terms "ADNF III" and "ADNP" refer to an activity dependent neurotrophic factor polypeptide having a predicted molecular weight of about 95 kDa (about 828 amino acid residues) and a pI of about 5.99. As described above, ADNF III polypeptides have an active site comprising an amino acid sequence of Asn-Ala-Pro-Val-Ser-Ile-Pro-Gln (also referred to as "NAPVSIPQ" or "NAP"; SEQ ID NO:2). See, Bassan et al., *J. Neurochem.* 72:1283-1293 (1999), incorporated herein by reference. Unless indicated as otherwise, "NAP" refers to a peptide having an amino acid sequence of Asn-Ala-Pro-Val-Ser-Ile-Pro-Gln (SEQ ID NO:2), not a peptide having an amino acid sequence of Asn-Ala-Pro.

The phrases "fetal alcohol syndrome" and "fetal alcohol effects" relate to various physical and mental conditions of an embryo, a fetus, or a subject who is exposed to alcohol in utero (e.g., whose mother consumed alcohol during pregnancy) in an amount sufficient to initiate the development of these conditions or to cause these conditions in the absence of prevention treatment, e.g., treatment with ADNF polypeptides. Some of these conditions include, but are not limited to, the following:

skeletal deformities: deformed ribs and sternum; curved spine; hip dislocations; bent, fused, webbed, or missing fingers or toes; limited movement of joints; small head;

facial abnormalities: small eye openings; skin webbing between eyes and base of nose; drooping eyelids; nearsightedness; failure of eyes to move in same direction; short upturned nose; sunken nasal bridge; flat or absent groove between nose and upper lip; thin upper lip; opening in roof of mouth; small jaw; low-set or poorly formed ears;

organ deformities: heart defects; heart murmurs; genital malformations; kidney and urinary defects; central nervous system handicaps: small brain; faulty arrangement of brain cells and connective tissue; mental retardation—usually mild to moderate, but occasionally severe; learning disabilities; short attention span; irritability in infancy; hyperactivity in childhood; poor body, hand, and finger coordination (see, e.g., www.well.com/user/woa/fsfas.htm); and other abnormalities: brain weight reduction, body weight reduction, a higher rate of death in utero, and a decrease in the level of VIP (e.g., VIP mRNA).

The phrase "reducing a condition associated with fetal alcohol syndrome" refers to reduction, including prevention, of parameters associated with fetal alcohol syndrome. Reduction is a change of a parameter by about 10% to about 100%, preferably at least about 50%, and more preferably at least about 80% compared to that of the control (e.g., exposed to alcohol in utero without any treatment, e.g., treatment with ADNF polypeptides). The parameters can be any physical or mental conditions listed above. For example, they can be: (1) a reduction in fetal viability in utero (e.g., the percentage of fetus death), (2) a reduction in fetal weights and fetal brain weights, (3) a reduction in the level of VIP (e.g., VIP mRNA) in embryos, (4) a learning deficit or decreased learning, (5) a reduction in the glutathione level.

The phrase "a subject with fetal alcohol syndrome" relates to an embryo, a fetus, or a subject, in particular a human, who is exposed to alcohol in utero and who has fetal alcohol syndrome or who is in danger of developing due to maternal alcohol consumption any of the conditions related to fetal alcohol syndrome, such as the effects described above.

The phrase "reducing neuronal cell death" refers to reduction, including prevention, of neuronal cell death. Reduction is a change of a parameter by about 10% to about 100%, preferably at least about 50%, and more preferably at least about 80% compared to that of the control (e.g., without treatment with, e.g., ADNF polypeptides). The reduction of neuronal cell death can be measured by any methods known in the art. For example, a mixture of ADNF I and ADNF III polypeptides that reduce neuronal cell death can be screened using the various methods described in U.S. Ser. No. 60/037,404, filed Feb. 27, 1997 (published as WO98/35042) and U.S. Ser. No. 09/187,330, filed Nov. 6, 1998, incorporated herein by reference. In addition, the assays described in the following references can also be used: Hill et al., *Brain Res.* 603, 222-233 (1993); Venner & Gupta, Nucleic Acid Res. 18, 5309 (1990); Peralta et al., *Nucleic Acid Res.* 18, 7162 (1990); Brenneman et al., *Nature* 335, 636 (1988); and Brenneman et al., *Dev. Brain Res.* 51:63 (1990); Forsythe & Westbrook, *J. Physiol. Lond.* 396:515 (1988). The teachings of these publications are hereby incorporated in their entirety by reference.

The term "contacting" is used herein interchangeably with the following: combined with, added to, mixed with, passed over, incubated with, flowed over, etc. Moreover, the ADNF polypeptides or nucleic acids encoding them of the present invention can be "administered" by any conventional method such as, for example, parenteral, oral, topical, and inhalation routes. In presently preferred embodiments, parenteral and nasal inhalation routes are employed. In the context of methods related to fetal alcohol syndrome, ADNF polypeptides can be administered directly to an embryo, a fetus, or a subject in utero or to the subject in utero indirectly, by administering the polypeptide to the mother by any other methods described herein.

"An amount sufficient" or "an effective amount" is that amount of a given ADNF polypeptide that reduces the neuronal cell death of interest or reduces fetal alcohol syndrome as described herein. For example, in the context of reducing fetal alcohol syndrome, "an amount sufficient" or "an effective amount" is that amount of a given ADNF polypeptide that reduces or prevents, for example, (1) the percentage of fetus death, (2) a reduction in fetal weights and fetal brain weights, or (3) a reduction in the level of VIP mRNA in embryos. In the context of neuronal death, "an amount sufficient" or "an effective amount" is that amount of a given ADNF polypeptide that reduces neuronal cell death in the assays of, e.g., Hill et al., *Brain Res.* 603, 222-233 (1993); Venner & Gupta, *Nucleic Acid Res.* 18, 5309 (1990); Peralta et al., *Nucleic Acid Res.* 18, 7162 (1990); Brenneman et al., *Nature* 335, 636 (1988); or Brenneman et al., *Dev. Brain Res.* 51:63 (1990); Forsythe & Westbrook *Physiol. Lond.* 396:515 (1988). The dosing range can vary depending on the ADNF polypeptide used, the route of administration and the potency of the particular ADNF polypeptide, but can readily be determined using the foregoing assays.

The term "biologically active" refers to a peptide sequence that will interact with naturally occurring biological molecules to either activate or inhibit the function of those molecules in vitro or in vivo. The term "biologically active" is most commonly used herein to refer to ADNF polypeptides or subsequences thereof that exhibit neuroprotective/neurotrophic action on neurons originating in the central nervous system either in vitro or in vivo. The neuroprotective/neurotrophic action of ADNF polypeptides can be tested using, e.g., cerebral cortical cultures treated with a neurotoxin (see, Gozes et al., *Proc. Nat'l. Acad. Sci. USA* 93:427-432 (1996)).

The terms "isolated," "purified," or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated ADNF nucleic acid is separated from open reading frames that flank the ADNF gene and encode proteins other than ADNF. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. The term nucleic acid is used interchangeably with gene, cDNA, mRNA, oligonucleotide, and polynucleotide.

The terms "polypeptide," "peptide," and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers.

The term "amino acid" refers to naturally occurring amino acids, amino acid analogs, and amino acid mimetics that function in a manner similar to the naturally occurring and analog amino acids. Naturally occurring amino acids are those encoded by the genetic code, as well as those amino acids that are later modified, e.g., hydroxyproline, γ-carboxyglutamate, and O-phosphoserine. Amino acid analogs refers to synthetic amino acids that have the same basic chemical structure as a naturally occurring amino acid, i.e., an α carbon that is bound to a hydrogen, a carboxyl group, an amino group, and an R group (e.g., homoserine, norleucine, methionine sulfoxide, methionine methyl sulfonium). Such analogs have modified R groups (e.g., norleucine) or modified peptide backbones, but retain the same basic chemical structure as a naturally occurring amino acid. Both naturally occurring and analog amino acids can be made synthetically. Amino acid mimetics refer to chemical compounds that have a structure that is different from the general chemical structure of an amino acid, but that function in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refer to those nucleic acids which encode identical or essentially identical amino acid sequences, or where the nucleic acid does not encode an amino acid sequence, to essentially identical sequences. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following groups each contain amino acids that are conservative substitutions for one another:

1) Alanine (A), Glycine (G);

2) Serine (S), Threonine (T);

3) Aspartic acid (D), Glutamic acid (E);

4) Asparagine (N), Glutamine (Q);

5) Cysteine (C), Methionine (M);

6) Arginine (R), Lysine (K), Histidine (H);

7) Isoleucine (I), Leucine (L), Valine (V); and

8) Phenylalanine (F), Tyrosine (Y), Tryptophan (W).

(see, e.g., Creighton, *Proteins* (1984)).

The terms "identical" or percent "identity," in the context of two or more nucleic acids or polypeptide sequences, refer to two or more sequences or subsequences that are the same or have a specified percentage of amino acid residues or nucleotides (i.e., 70% identity) that are the same, when compared and aligned for maximum correspondence over a comparison window, as measured using one of the following sequence comparison algorithms or by manual alignment and visual inspection. Such sequences are then said to be "substantially identical." This definition also refers to the complement of a test sequence. Preferably, the percent identity exists over a region of the sequence that is at least about 25 amino acids in length, more preferably over a region that is 50 or 100 amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with a wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C.

A positive hybridization is at least twice background. Those of ordinary skill will readily recognize that alternative hybridization and wash conditions can be utilized to provide conditions of similar stringency.

DETAILED DESCRIPTION OF THE INVENTION AND PREFERRED EMBODIMENTS

I. Introduction

It has now been discovered that polypeptides derived from the neurotrophic proteins ADNF I and ADNF III are effective for reducing a condition associated with fetal alcohol syndrome in a subject who is exposed to alcohol in utero. In one embodiment, it has been found that treatment with a mixture of an ADNF I polypeptide and an ADNF III polypeptide has a remarkable synergistic effect in reducing or preventing a condition associated with fetal alcohol syndrome. In addition, it has now been discovered that a mixture of an ADNF I polypeptide and an ADNF III polypeptide is effective for reducing neuronal cell death.

As such, the present invention provides, inter alia, a method for reducing a condition associated with fetal alcohol syndrome in a subject who is exposed to alcohol in utero with an ADNF polypeptides (e.g., ADNF I polypeptides, ADNF III polypeptides, mixtures of ADNF I and ADNF III polypeptides). The present invention also provides a method for reducing neuronal cell death by contacting neuronal cells with a mixture of ADNF I and ADNF III polypeptides in an amount sufficient to reduce neuronal cell death. Still further, the present invention provides a pharmaceutical composition comprising a pharmaceutically acceptable excipient and a mixture of ADNF I and ADNF III polypeptides.

In addition, the ADNF polypeptides of the present invention can be used to treat numerous forms of neurodegeneration (see Lipton & Rosenberg, *New Eng. J. Med.* 330:613-622 (1994), the teaching of which are incorporated herein by reference for all purposes). Such neurodegeneration includes, but is not limited to, the following: Huntington's disease; AIDS dementia complex; neuropathic pain syndromes; olivopontocerebellar atrophy; parkinsonism and Parkinson's disease; amyotrophic lateral sclerosis; mitochondrial abnormalities and other inherited or acquired biochemical disorders; MELAS syndrome; MERRF; Leber's disease; Wernicke's encephalopathy; Rett syndrome; homocysteinuria; hyperprolinemia; nonketotic hyperglycinemia; hydroxybutyric aminoaciduria; sulfite oxide deficiency; combined systems disease; lead encephalopathy; Alzheimer's disease; hepatic encephalopathy; Tourette's syndrome; Down's syndrome; developmental retardation and learning impairments; closed head trauma; dopamine toxicity; drug addiction, tolerance, and dependency. Those of skill in the art will appreciate that the above list is merely illustrative and that the ADNF polypeptides of the present invention can be used to treat other neurological disorders.

II. Methods for Reducing Fetal Alcohol Syndrome

The present invention provides a method for reducing a condition associated with fetal alcohol syndrome in a subject who is exposed to alcohol in utero. The method comprises administering to the subject an ADNF polypeptide in an amount sufficient to reduce the condition associated with fetal alcohol syndrome. An ADNF polypeptide can be directly administered to the embryo, fetus, or subject. Alternatively, an ADNF polypeptide can be indirectly administered to the fetus by administering it to the mother.

In one aspect, the method comprises administering an ADNF I polypeptide that comprises an active core site having the following amino acid sequence: Ser-Ala-Leu-Leu-Arg-Ser-Ile-Pro-Ala (SEQ ID NO:1). In one embodiment, the ADNF I polypeptide consists of an active core site that has an amino acid sequence of Ser-Ala-Leu-Leu-Arg-Ser-Ile-Pro-Ala (SEQ ID NO:1). In another embodiment, the ADNF I polypeptide can comprise additional amino acids at the N-terminus and/or at the C-terminus of the active core site. For example, the ADNF I polypeptide can comprise up to 40 amino acids at the N-terminus and/or the C-terminus of the active core site. In another example, the ADNF I polypeptide can comprise up to 20 amino acids at the N-terminus and/or the C-terminus of the active core site. In yet another example, the ADNF I polypeptide can comprise up to 10 amino acids at the N-terminus and/or the C-terminus of the active core site. In yet another embodiment, the ADNF I polypeptide can be a full length ADNF I polypeptide.

In another aspect, the method comprises administering to the subject an ADNF III polypeptide that comprises an active core site having the following amino acid sequence: Asn-Ala-Pro-Val-Ser-Ile-Pro-Gln (SEQ ID NO:2). In one embodiment, the ADNF I polypeptide consists of an active core site that has an amino acid sequence of Asn-Ala-Pro-Val-Ser-Ile-Pro-Gln (SEQ ID NO:2). In another embodiment, the ADNF III polypeptide can comprise additional amino acids at the N-terminus and/or at the C-terminus of the active core site. For example, the ADNF III polypeptide can comprise up to 40 amino acids at the N-terminus and/or the C-terminus of the active core site. In another example, the ADNF III polypeptide can comprise up to 20 amino acids at the N-terminus and/or the C-terminus of the active core site. In yet another example, the ADNF III polypeptide can comprise up to 10 amino acids at the N-terminus and/or the C-terminus of the active core site. In yet another embodiment, the ADNF III polypeptide can be a full length ADNF III polypeptide.

In a preferred embodiment, the ADNF I polypeptide comprises an amino acid sequence of $(R^1)_x$-Ser-Ala-Leu-Leu-Arg-Ser-Ile-Pro-Ala-$(R^2)_y$ (SEQ ID NO:3), and the ADNF III polypeptide comprises an amino acid sequence of $(R^3)_w$-Asn-Ala-Pro-Val-Ser-Ile-Pro-Gln-$(R^4)_z$ (SEQ ID NO:4).

In the above formula, each of $R^1$, $R^2$, $R^3$, and $R^4$, if present, is an amino acid sequence comprising from 1 to about 40 amino acids wherein each amino acid is independently selected. The term "independently selected" is used herein to indicate that the amino acids making up, for example, the amino acid sequence $R^1$ may be identical or different (e.g., all of the amino acids in the amino acid sequence may be threonine, etc.). Moreover, as previously explained, the amino acids making up the amino acid sequence $R^1$ may be either naturally occurring amino acids, or known analogues of natural amino acids that functions in a manner similar to the naturally occurring amino acids (i.e., amino acid mimetics). This discussion pertaining to $R^1$ is fully applicable to $R^2$, $R^3$, and $R^4$.

Within the above formula for the ADNF I polypeptide, x and y are independently selected and are equal to zero or one. The term independently selected is used herein to indicate that x and y may be identical or different. For example, x and y may both be zero or, alternatively, x and y may both be one. In addition, x may be zero and y may be one or, alternatively, x may be one and y may be zero. Moreover, if x and y are both one, the amino acid sequences $R^1$ and $R^2$ may be the same or different. As such, the amino acid sequences $R^1$ and $R^2$ are independently selected. If $R^1$ and $R^2$ are the same, they are identical in terms of both chain length and amino acid composition. For example, both $R^1$ and $R^2$ may be Val-Leu-Gly-Gly-Gly (SEQ ID NO:5); see SEQ ID NO:14. If $R^1$ and $R^2$ are different, they can differ from one another in terms of chain length and/or amino acid composition and/or order of amino acids in the amino acids sequences. For example, $R^1$ may be Val-Leu-Gly-Gly-Gly (SEQ ID NO:5), whereas $R^2$ may be Val-Leu-Gly-Gly (SEQ ID NO:9); see SEQ ID NO:15. Alternatively, $R^1$ may be Val-Leu-Gly-Gly-Gly (SEQ ID NO:5), whereas $R^2$ may be Val-Leu-Gly-Gly-Val (SEQ ID NO:10); see SEQ ID NO:16. Alternatively, $R^1$ may be Val-Leu-Gly-Gly-Gly (SEQ ID NO:5), whereas $R^2$ may be Gly-Val-Leu-Gly-Gly (SEQ ID NO:11); see SEQ ID NO:17).

Similarly, w and z are independently selected and are equal to zero or one within the above formula for the ADNF III polypeptide. The term independently selected is used herein to indicate that w and z may be identical or different. For example, w and z may both be zero or, alternatively, w and z may both be one. In addition, w may be zero and z may be one or, alternatively, w may be one and z may be zero. Moreover, if w and z are both one, the amino acid sequences $R^3$ and $R^4$ may be the same or different. As such, the amino acid sequences $R^3$ and $R^4$ are independently selected. If $R^3$ and $R^4$ are the same, they are identical in terms of both chain length and amino acid composition. For example, both $R^3$ and $R^4$ may be Leu-Gly-Leu-Gly-Gly (SEQ ID NO:7); see SEQ ID NO:18. If $R^3$ and $R^4$ are different, they can differ from one another in terms of chain length and/or amino acid composition and/or order of amino acids in the amino acids sequences. For example, $R^3$ may be Leu-Gly-Leu-Gly-Gly (SEQ ID NO:7), whereas $R^4$ may be Leu-Gly-Leu-Gly (SEQ ID NO:12); see SEQ ID NO:19. Alternatively, $R^3$ may be Leu-Gly-Leu-Gly-Gly (SEQ ID NO:7), whereas $R^4$ may be Leu-Gly-Leu-Gly-Leu (SEQ ID NO:13); see SEQ ID NO:20.

Within the scope, certain ADNF I and ADNF III polypeptides are preferred, namely those in which x, y, w, and z are all zero (i.e., SALLRSIPA (SEQ ID NO:1) and NAPVSIPQ (SEQ ID NO:2), respectively). Equally preferred are ADNF I polypeptides in which x is one; $R^1$ is Val-Leu-Gly-Gly-Gly (SEQ ID NO:5); and y is zero; see SEQ ID NO:21. Also equally preferred are ADNF I polypeptides in which x is one; $R^1$ is Val-Glu-Glu-Gly-Ile-Val-Leu-Gly-Gly-Gly (SEQ ID NO:6); and y is zero; see SEQ ID NO:22. Also equally preferred are ADNF III polypeptides in which w is one; $R^3$ is Gly-Gly; and z is zero; see SEQ ID NO:23. Also equally preferred are ADNF III polypeptides in which w is one; $R^3$ is Leu-Gly-Gly; z is one; and $R^4$ is Gln-Ser; see SEQ ID NO:24. Also equally preferred are ADNF III polypeptides in which w is one; $R^3$ is Leu-Gly-Leu-Gly-Gly-(SEQ ID NO:7); z is one; and $R^4$ is Gln-Ser; see SEQ ID NO:25. Also equally preferred are ADNF III polypeptides in which w is one; $R^3$ is Ser-Val-Arg-Leu-Gly-Leu-Gly-Gly (SEQ ID NO:8); z is one; and $R^4$ is Gln-Ser; see SEQ ID NO:26. Additional amino acids can be added to both the N-terminus and the C-terminus of these active sites (SALLRSIPA (SEQ ID NO:1) or NAPVSIPQ (SEQ ID NO:2)) without loss of biological activity as evidenced by the fact that the intact ADNF I or ADNF III growth factors exhibit extraordinary biological activity. See, U.S. Ser. No. 08/324,297, filed Oct. 17, 1994 (also published as WO96/11948) for the description of ADNF I polypeptides; and U.S. Ser. No. 60/037,404 filed Feb. 27, 1997 and U.S. Ser. No. 60/059,621 filed, Sep. 23, 1997 (also published as WO98/35042) for the description of ADNF III polypeptides, all of which are incorporated herein by reference.

In yet another aspect, the method comprises administering to the subject a mixture of an ADNF I polypeptide and an ADNF III polypeptide. Any one or more of the ADNF I polypeptides described herein can be mixed with any one or more of the ADNF III polypeptides described herein. A mixture of an ADNF I polypeptide and an ADNF III polypeptide can be a blend of two or more of these polypeptides. A mixture of an ADNF I polypeptide and an ADNF III polypeptide can also refer to one or more of ADNF I polypeptides that are coupled (directly or indirectly) to one or more of ADNF III polypeptides. For example, an ADNF I polypeptide can be covalently linked to an ADNF III polypeptide. A mixture of ADNF I polypeptides and ADNF III polypeptides can be prepared as a single composition and can be administered to a subject. Alternatively, an ADNF I polypeptide and an ADNF III polypeptide can be prepared as separate compositions. The separate compositions can then be administered simultaneously or sequentially to the subject. Furthermore, different proportions of an ADNF I polypeptide and an ADNF III polypeptide can be administered to a subject. For example, the subject can be administered with ADNF polypeptides, wherein the ratio of an ADNF I polypeptide and an ADNF III polypeptide can be in the range of 1:100 to 100:1, 1:10 to 10:1, or 1:2 to 2:1.

In yet another aspect, other ADNF polypeptide (including their alleles, polymorphic variants, species homologs and subsequences thereof) can be used to reduce a condition associated with fetal alcohol syndrome. These other ADNF polypeptides can be obtained by screening candidate ADNF polypeptides using a well-characterized animal model for FAS. For example, the C57B1/6J mouse strain can be used. Previous work with this strain has defined the effects of dosage and embryonic timing on maternal serum alcohol levels and embryonic effects (Webster et al., *Neurobehav. Tox.*, 2:227-34 (1980), incorporated herein by reference). Intraperitoneal treatment allows for defined and reproducible dosages. Acute (single) dosages of alcohol can reproduce the phenotype of FAS (Webster et al., (1980), supra). Treatment on E8 results in the highest rate of fetal anomalies and demises. Also, vasoactive intestinal peptide's growth regulating effects on the embryo are limited to the early post-implantation period of embryogenesis. Thus, E8 can be chosen as a stage for screening neuroprotective ADNF polypeptides. For example, mice can be injected with 25% ethyl alcohol in saline (v/v) or vehicle alone at, e.g., 0.030 ml/g maternal body weight at, e.g., 9:00 a.m. on E8 (embryonic gestation day 8). ADNF polypeptides can be screened by pretreating the mice 30 minutes prior to alcohol administration. In one embodiment, the dose for nasal administration for an ADNF polypeptide is about 1 µg-50 µg, preferably about 1 µg-10 µg/mouse. This dose is based on the average body weight of mice, and an appropriate dose for human can be extrapolated based on the average body weight of human.

Various parameters can be measured to determine if an ADNF polypeptide or a mixture of ADNF polypeptides reduces a condition associated with fetal alcohol syndrome. For example, the degree of learning deficits can be compared between the control (e.g., untreated with ADNF polypeptides) and a group pretreated with ADNF polypeptides. Learning deficits can be assessed using, for example, a Morris water maze (see, e.g., the Example section). In another example, a number of fetal demises (i.e., death) or fetal vitality can be compared between the control and a group pretreated with ADNF polypeptides. In yet another example, the fetal weight and fetal brain weight in the surviving fetuses, e.g., at E18, can be compared. In yet another example, the level of VIP (e.g., mRNA or protein) can be compared between the control and a group treated with ADNF polypeptides. In yet another example, the glutathione level in the control and the pretreated group can be compared. If any one or more of these parameters are reduced for the group treated with ADNF polypeptides by, e.g., about 10% to about 100%, optionally at least about 50% or 80% compared to control, then these ADNF polypeptides can be advantageously used in the present invention.

III. Methods for Reducing Neuronal Cell Death

In another aspect, the present invention provides a method for reducing neuronal cell death, the method comprising contacting neuronal cells with a mixture of an ADNF I polypeptide and an ADNF III polypeptide in an amount sufficient to reduce neuronal cell death.

In one embodiment, the method comprises contacting neuronal cells with a mixture of an ADNF I polypeptide and an ADNF III polypeptide, wherein the ADNF I polypeptide has an active core site having the amino acid sequence of Ser-Ala-Leu-Leu-Arg-Ser-Ile-Pro-Ala (SEQ ID NO:1), and wherein the ADNF III polypeptide has an active core site having the amino acid sequence of Asn-Ala-Pro-Val-Ser-Ile-Pro-Gln (SEQ ID NO:2). In another embodiment, the ADNF I polypeptide can consist of an active core site having the amino acid sequence of Ser-Ala-Leu-Leu-Arg-Ser-Ile-Pro-Ala (SEQ ID NO:1) and/or the ADNF III polypeptide can consist of an active core site having the amino acid sequence of Asn-Ala-Pro-Val-Ser-Ile-Pro-Gln (SEQ ID NO:2). In yet another embodiment, the ADNF I polypeptide and/or the ADNF III polypeptide can comprise additional amino acids at the N-terminus and/or at the C-terminus of their respective active core sites. For example, the ADNF I polypeptide and/or the ADNF III polypeptide can have up to 40 amino acids at the N-terminus and/or the C-terminus of their respective active core sites. In another example, the ADNF I polypeptide and/or the ADNF III polypeptide can have up to 20 amino acids at the N-terminus and/or the C-terminus of their respective active core sites. In yet another example, the ADNF I polypeptide and/or the ADNF III polypeptide can have up to 10 amino acids at the N-terminus and/or the C-terminus of their respective active core site. In certain embodiments, these additional amino acids are present at both the N-terminus and the C-terminus of the active core site of the ADNF polypeptides. In yet another example, the ADNF I polypeptide can be a full length polypeptide, and/or the ADNF III polypeptide can be a full length polypeptide.

In a preferred embodiment, the ADNF I polypeptide comprises an amino acid sequence of $(R^1)_x$-Ser-Ala-Leu-Leu-Arg-Ser-Ile-Pro-Ala-$(R^2)_y$ (SEQ ID NO:3), and the ADNF III polypeptide comprises an amino acid sequence of $(R^3)_w$-Asn-Ala-Pro-Val-Ser-Ile-Pro-Gln-$(R^4)_z$ (SEQ ID NO:4). In another embodiment, x and y are both zero for the above formula for the ADNF I polypeptide (SEQ ID NO:1), and w and z are both zero for the above formula for the ADNF III polypeptide (SEQ ID NO:2). The previous discussion pertaining to $R^1$, $R^2$, $R^3$, $R^4$, x, y, and w and z, and various preferred ADNF polypeptide embodiments is fully applicable to the ADNF polypeptides used in this method of present invention and, thus, will not be repeated with respect to this particular method.

In this and other aspects of the invention, any one or more of the ADNF I polypeptide described herein can be mixed with any one or more of the ADNF III polypeptide described herein. A mixture of an ADNF I polypeptide and an ADNF III polypeptide can be a blend of two or more of these polypeptides. A mixture of an ADNF I polypeptide and an ADNF III polypeptide can also refer to one or more of ADNF I polypeptides that are coupled to one or more of ADNF III polypeptides. For example, an ADNF I polypeptide can be covalently linked to an ADNF III polypeptide. A mixture of an ADNF I polypeptide and an ADNF III polypeptide can be prepared as a single composition and can be contacted with neuronal cells. Alternatively, an ADNF I polypeptide and an ADNF III polypeptide can be prepared as separate compositions and can be contacted simultaneously or sequentially with neuronal cells. Furthermore, different proportions of an ADNF I polypeptide and an ADNF III polypeptide can be contacted with neuronal cells. For example, in a mixture the ratio of an ADNF I polypeptide and an ADNF III polypeptide can be in the range of 1:100 to 100:1, 1:10 to 10:1, or 1:2 to 2:1.

A mixture of ADNF I and ADNF III polypeptides of the present invention can be used in the treatment of neurological deficiencies and for the prevention of neuronal cell death. For example, a mixture of ADNF I and ADNF III polypeptides can be used to prevent the death of neuronal cells including, but not limited to, spinal cord neurons, hippocampal neurons, cerebral cortical neurons and cholinergic neurons. More particularly, a mixture of ADNF I and ADNF III polypeptides of the present invention can be used in the prevention of cell death associated with (1) gp120, the envelope protein from HIV; (2) N-methyl-D-aspartic acid (excito-toxicity); (3) tetrodotoxin (blockage of electrical activity); and (4) β-amyloid peptide, a substance related to neuronal degeneration in Alzheimer's disease. Similarly, it will be readily apparent to those of skill in the art that a mixture of ADNF I and ADNF III polypeptides of the present invention can be used in a similar manner to prevent neuronal cell death associated with a number of other neurological diseases and deficiencies. Pathologies that would benefit from therapeutic and diagnostic applications of this invention include conditions (diseases and insults) leading to neuronal cell death and/or sub-lethal neuronal pathology including, for example, the following:

diseases of central motor systems including degenerative conditions affecting the basal ganglia (Huntington's disease, Wilson's disease, striatonigral degeneration, corticobasal ganglionic degeneration), Tourette's syndrome, Parkinson's disease, progressive supranuclear palsy, progressive bulbar palsy, familial spastic paraplegia, spinomuscular atrophy, ALS and variants thereof, dentatorubral atrophy, olivo-pontocerebellar atrophy, paraneoplastic cerebellar degeneration, and dopamine toxicity;

diseases affecting sensory neurons such as Friedreich's ataxia, diabetes, peripheral neuropathy, retinal neuronal degeneration;

diseases of limbic and cortical systems such as cerebral amyloidosis, Pick's atrophy, Retts syndrome;

neurodegenerative pathologies involving multiple neuronal systems and/or brainstem including Alzheimer's disease, AIDS-related dementia, Leigh's disease, diffuse Lewy body disease, epilepsy, multiple system atrophy, Guillain-Barre syndrome, lysosomal storage disorders such as lipofuscinosis, late-degenerative stages of Down's syndrome, Alper's disease, vertigo as result of CNS degeneration;

pathologies associated with developmental retardation and learning impairments, and Down's syndrome, and oxidative stress induced neuronal death;

pathologies arising with aging and chronic alcohol or drug abuse including, for example, with alcoholism the degeneration of neurons in locus coeruleus, cerebellum, cholinergic basal forebrain; with aging degeneration of cerebellar neurons and cortical neurons leading to cognitive and motor impairments; and with chronic amphetamine abuse degeneration of basal ganglia neurons leading to motor impairments;

pathological changes resulting from focal trauma such as stroke, focal ischemia, vascular insufficiency, hypoxic-ischemic encephalopathy, hyperglycemia, hypoglycemia, closed head trauma, or direct trauma;

pathologies arising as a negative side-effect of therapeutic drugs and treatments (e.g., degeneration of cingulate and entorhinal cortex neurons in response to anticonvulsant doses of antagonists of the NMDA class of glutamate receptor).

Other mixtures of ADNF I and ADNF III polypeptides (including their alleles, polymorphic variants, species homologs and subsequences thereof) that reduce neuronal cell death can be screened using the various methods described in U.S. Ser. No. 60/037,404, filed Feb. 27, 1997 (published as WO98/35042), and U.S. Ser. No. 09/187,330 filed Nov. 6, 1998, both of which are incorporated herein by reference. For example, it will be readily apparent to those skilled in the art that using the teachings set forth above with respect to the design and synthesis of ADNF polypeptides and the assays described herein, one of ordinary skill in the art can identify other mixtures of ADNF polypeptides which can reduce neuronal cell death. For example, Brenneman et al., *Nature* 335, 636 (1988), and Dibbern et al., *J. Clin. Invest.* 99:2837-2841 (1997), incorporated herein by reference, teach assays that can be used to screen mixtures of ADNF I and ADNF III polypeptides that are capable of reducing neuronal cell death associated with envelope protein (gp120) from HIV. Also, Brenneman et al., *Dev. Brain Res.* 51:63 (1990), and Brenneman & Gozes, *J. Clin. Invest.* 97:2299-2307 (1996), incorporated herein by reference, teach assays that can be used to screen mixtures of ADNF I and ADNF III polypeptides which are capable of reducing neuronal cell death associated with excito-toxicity induced by stimulation by N-methyl-D-asparate. Furthermore, Venner & Gupta, *Nucleic Acid Res.* 18, 5309 (1990) and Peralta et al., *Nucleic Acid Res.* 18, 7162 (1990), incorporated herein by reference, teach assays that can be used to screen mixtures of ADNF I and ADNF III polypeptides which are capable of reducing TTX-induced neuronal cell death. Other assays described in, e.g., WO98/35042 can be used to identify ADNF polypeptides which can be used to reduce neuronal cell death associated with other clinical conditions.

Moreover, mixtures of ADNF I and ADNF III polypeptides that reduce neuronal cell death can be screened in vivo. For example, the ability of mixtures of ADNF I and ADNF III polypeptides that can protect against learning and memory deficiencies associated with cholinergic blockade can be tested. For example, cholinergic blockade can be obtained in rats by administration of the cholinotoxin AF64A, and a mixture of ADNF I and ADNF III polypeptides can be administered intranasally and the water maze experiments can be performed (Gozes et al., *Proc. Natl. Acad. Sci. USA* 93:427-432 (1996), the teachings of which are incorporated herein by reference). Animals treated with an efficacious mixture of ADNF I and ADNF III polypeptides would show improvement in their learning and memory capacities compared to the control.

Furthermore, the ability of mixtures of ADNF I and ADNF III polypeptides that can protect or reduce neuronal cell death associated with Alzheimer's disease can be screened in vivo. For these experiments, apolipoprotein E (ApoE)-deficient homozygous mice can be used (Plump et al., *Cell* 71:343-353 (1992); Gordon et al., *Neuroscience Letters* 199:1-4 (1995); Gozes et al., *J. Neurobiol.* 33:329-342 (1997)), the teachings of which are incorporated herein by reference.

In the above assays, various permutations of ADNF I and ADNF III polypeptides can be mixed to determine a mixture which provides the best result in terms of reduction of neuronal cell death. In each mixture, the proportion of ADNF I and ADNF III polypeptides can be equal or different. The proportion of ADNF I and ADNF III polypeptides can be adjusted until mixtures which provide the most efficacious formulations in reducing neuronal cell death are found. In these assays, a blend of ADNF I and ADNF III polypeptides or physically coupled ADNF I and ADNF III polypeptides can be used. Alternatively, an ADNF I polypeptide and an ADNF III polypeptide can be added sequentially in an assay.

If any one or more of these parameters are reduced for the pretreated group by, e.g., about 10% to about 100%, optionally at least about 50% or 80% compared to control, then these other ADNF polypeptides can be advantageously used in the present methods.

IV. Pharmaceutical Compositions

In still yet another aspect, the present invention provides pharmaceutical compositions comprising one of the previously described mixtures of ADNF I and ADNF III polypeptides in an amount sufficient to exhibit neuroprotective/neurotrophic activity, and a pharmaceutically acceptable diluent, carrier or excipient.

In one embodiment, the pharmaceutical composition comprises a mixture of an ADNF I polypeptide and an ADNF III polypeptide, wherein the ADNF I polypeptide has an active core site having the amino acid sequence of Ser-Ala-Leu-Leu-Arg-Ser-Ile-Pro-Ala (SEQ ID NO:1), and wherein the ADNF III polypeptide has an active core site having the amino acid sequence of Asn-Ala-Pro-Val-Ser-Ile-Pro-Gln (SEQ ID NO:2). In another embodiment, the pharmaceutical composition comprises a mixture of an ADNF I polypeptide and an ADNF III polypeptide, wherein an ADNF I polypeptide consists of an active core site having the amino acid sequence of Ser-Ala-Leu-Leu-Arg-Ser-Ile-Pro-Ala (SEQ ID NO:1) and/or an ADNF III polypeptide consists of an active core site having the amino acid sequence of Asn-Ala-Pro-Val-Ser-Ile-Pro-Gln (SEQ ID NO:2). In yet another embodiment, the pharmaceutical composition comprises ADNF polypeptide mixtures, wherein an ADNF I polypeptide and/or an ADNF III polypeptide comprises additional amino acids at the N-terminus and/or at the C-terminus of their respective active core sites. For example, an ADNF I polypeptide and/or an ADNF III polypeptide can have up to 40 amino acids at the N-terminus and/or the C-terminus of their respective active core sites. In another example, an ADNF I polypeptide and/or an ADNF III polypeptide can have up to 20 amino acids at the N-terminus and/or the C-terminus of their respective active core sites. In yet another example, an ADNF I polypeptide and/or an ADNF III polypeptide can have up to 10 amino acids at the N-terminus and/or the C-terminus of their respective active core site. In certain embodiments, additional amino acids can be present at both at the N-terminus and the C-terminus of the active core site of the ADNF polypeptides. In yet another example, the ADNF I polypeptide can be a full length polypeptide, and/or the ADNF III polypeptide can be a full length polypeptide.

In a preferred embodiment, the pharmaceutical composition comprises ADNF polypeptide mixtures, wherein the ADNF I polypeptide comprises an amino acid sequence of $(R^1)_x$-Ser-Ala-Leu-Leu-Arg-Ser-Ile-Pro-Ala-$(R^2)_y$ (SEQ ID NO:3), and the ADNF III polypeptide comprises an amino acid sequence of $(R^3)_w$-Asn-Ala-Pro-Val-Ser-Ile-Pro-Gln-$(R^4)_z$ (SEQ ID NO:4). In another embodiment, x and y are both zero for the above formula for the ADNF I polypeptide (SEQ ID NO:1), and w and z are both zero for the above formula for the ADNF III polypeptide (SEQ ID NO:2). The previous discussion pertaining to $R^1$, $R^2$, $R^3$, $R^4$, x, y, and w and z, and various preferred ADNF polypeptide embodiments is fully applicable to the ADNF polypeptides used in this aspect of present invention and, thus, will not be repeated with respect to this aspect of the invention.

In a pharmaceutical composition, any one or more of the ADNF I polypeptide described herein can be mixed with any one or more of the ADNF III polypeptide described herein. A mixture of an ADNF I polypeptide and an ADNF III polypeptide can be a blend of two or more of these polypeptides. A mixture of an ADNF I polypeptide and an ADNF III polypeptide can also refer to one or more of ADNF I polypeptides that are coupled to one or more of ADNF III polypeptides. For example, an ADNF I polypeptide can be covalently linked to an ADNF III polypeptide. A mixture of an ADNF I polypeptide and an ADNF III polypeptide can be prepared as a single composition and can be administered to a subject. Alternatively, an ADNF I polypeptide and an ADNF III polypeptide can be prepared as separate compositions and can be administered simultaneously or sequentially to a subject. Furthermore, different proportions of an ADNF I polypeptide and an ADNF III polypeptide can be administered to a subject. For example, in a mixture the ratio of an ADNF I polypeptide and an ADNF III polypeptide can be in the range of 1:100 to 100:1, 1:10 to 10:1, or 1:2 to 2:1.

The pharmaceutical compositions of the present invention are suitable for use in a variety of drug delivery systems. Suitable formulations for use in the present invention are found in *Remington's. Pharmaceutical Sciences* (17th ed. 1985)), which is incorporated herein by reference. In addition, for a brief review of methods for drug delivery, see Langer, *Science* 249:1527-1533 (1990), which is incorporated herein by reference.

Due to their ability to increase growth and survival of neurons, a mixture of ADNF I and ADNF III polypeptides has extensive uses in the treatment of neurological deficiencies that result, for example, from neuronal development, aging, neurodegenerative diseases or spinal cord injury. As such, the present invention provides for therapeutic compositions or medicaments comprising a mixture of one or more of the ADNF I and ADNF III polypeptides described herein above in mixture with a pharmaceutically acceptable excipient, wherein the amount of a mixture the ADNF I and ADNF III polypeptide is sufficient to provide a desirable therapeutic effect.

Small polypeptides including SALLRSIPA (SEQ ID NO:1) and NAPVSIPQ (SEQ ID NO:2) cross the blood brain barrier. For longer polypeptides that do not the cross blood brain barrier, methods of administering proteins to the brain are well known. For example, proteins, polypeptides, other compounds and cells can be delivered to the mammalian brain via intracerebroventricular (ICV) injection or via a cannula (see, e.g., Motta & Martini, *Proc. Soc. Exp. Biol. Med.* 168:62-64 (1981); Peterson et al., *Biochem. Pharamacol.* 31:2807-2810 (1982); Rzepczynski et al., *Metab. Brain Dis.* 3:211-216 (1988); Leibowitz et al., *Brain Res. Bull.* 21:905-912 (1988); Sramka et al., *Stereotact. Funct. Neurosurg.* 58:79-83 (1992); Peng et al., *Brain Res.* 632:57-67 (1993); Chem et al., *Exp. Neurol.* 125:72-81 (1994); Nikkhah et al., *Neuroscience* 63:57-72 (1994); Anderson et al., *J. Comp. Neurol.* 357:296-317 (1995); and Brecknell & Fawcett, *Exp. Neurol.* 138:338-344 (1996)). In particular, cannulas can be used to administer neurotrophic factors to mammals (see, e.g., Motta & Martini, *Proc. Soc. Exp. Biol. Med.* 168:62-64 (1981) (neurotensin); Peng et al., *Brain Res.* 632:57-67 (1993) (NGF); Anderson et al., *J. Comp. Neurol.* 357:296-317 (1995) (BDNF, NGF, neurotrophin-3).

Alternatively, longer ADNF polypeptides that do not cross blood brain barrier can be coupled with a material which assists the ADNF polypeptide to cross the blood brain barrier and to traverse the plasma membrane of a cell, or the membrane of an intra-cellular compartment such as the nucleus. Cellular membranes are composed of lipid-protein bilayers that are freely permeable to small, nonionic lipophilic compounds and are inherently impermeable to polar compounds, macromolecules, and therapeutic or diagnostic agents. However, proteins and other compounds such as liposomes have been described, which have the ability to translocate polypeptides such as ADNF polypeptides across a cell membrane.

For example, "membrane translocation polypeptides" have amphiphilic or hydrophobic amino acid subsequences that have the ability to act as membrane-translocating carriers. In one embodiment, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, *Current Opinion in Neurobiology* 6:629-634 (1996)). Another subsequence, the hydrophobic domain of signal peptides, was found to have similar cell membrane translocation characteristics (see, e.g., Lin et al., *J. Biol. Chem.* 270:1 4255-14258 (1995)).

Examples of peptide sequences which can be linked to a ADNF polypeptide of the invention, for facilitating uptake of ADNF polypeptides into cells, include, but are not limited to: an 11 amino acid peptide of the tat protein of HIV (see Schwarze et al., *Science* 285:1569-1572 (1999)); a 20 residue peptide sequence which corresponds to amino acids 84-103 of the p16 protein (see Fahraeus et al., *Current Biology* 6:84 (1996)); the third helix of the 60-amino acid long homeodomain of Antennapedia (Derossi et al., *J. Biol. Chem.* 269: 10444 (1994)); the h region of a signal peptide such as the Kaposi fibroblast growth factor (K-FGF) h region (Lin et al., supra); or the VP22 translocation domain from HSV (Elliot & O'Hare, *Cell* 88:223-233 (1997)). Other suitable chemical moieties that provide enhanced cellular uptake may also be chemically linked to ADNF polypeptides.

Toxin molecules also have the ability to transport polypeptides across cell membranes. Often, such molecules are composed of at least two parts (called "binary toxins"): a translocation or binding domain or polypeptide and a separate toxin domain or polypeptide. Typically, the translocation domain or polypeptide binds to a cellular receptor, and then the toxin is transported into the cell. Several bacterial toxins, including *Clostridium perfringens* iota toxin, diphtheria toxin (DT), *Pseudomonas* exotoxin A (PE), pertussis toxin (PT), *Bacillus anthracis* toxin, and pertussis adenylate cyclase (CYA), have been used in attempts to deliver peptides to the cell cytosol as internal or amino-terminal fusions (Arora et al., *J. Biol. Chem.*, 268:3334-3341 (1993); Perelle et al., *Infect. Immun.*, 61:5147-5156 (1993); Stenmark et al., *J. Cell Biol.* 113:1025-1032 (1991); Donnelly et al., *PNAS* 90:3530-3534 (1993); Carbonetti et al., *Abstr. Annu. Meet. Am. Soc. Microbiol.* 95:295 (1995); Sebo et al., *Infect. Immun.* 63:3851-3857 (1995); Klimpel et al., *PNAS U.S.A.* 89:10277-10281 (1992); and Novak et al., *J. Biol. Chem.* 267:17186-17193 1992)).

Such subsequences can be used to translocate ADNF polypeptides across a cell membrane. ADNF polypeptides can be conveniently fused to or derivatized with such sequences. Typically, the translocation sequence is provided as part of a fusion protein. Optionally, a linker can be used to link the ADNF polypeptides and the translocation sequence. Any suitable linker can be used, e.g., a peptide linker.

The ADNF polypeptides can also be introduced into an animal cell, preferably a mammalian cell, via a liposomes and liposome derivatives such as immunoliposomes. The term "liposome" refers to vesicles comprised of one or more concentrically ordered lipid bilayers, which encapsulate an aqueous phase. The aqueous phase typically contains the compound to be delivered to the cell, i.e., an ADNF polypeptide.

The liposome fuses with the plasma membrane, thereby releasing the ADNF polylpeptides into the cytosol. Alternatively, the liposome is phagocytosed or taken up by the cell in a transport vesicle. Once in the endosome or phagosome, the liposome either degrades or fuses with the membrane of the transport vesicle and releases its contents.

In current methods of drug delivery via liposomes, the liposome ultimately becomes permeable and releases the encapsulated compound (in this case, an ADNF polypeptide) at the target tissue or cell. For systemic or tissue specific delivery, this can be accomplished, for example, in a passive manner wherein the liposome bilayer degrades over time through the action of various agents in the body. Alternatively, active drug release involves using an agent to induce a permeability change in the liposome vesicle. Liposome membranes can be constructed so that they become destabilized when the environment becomes acidic near the liposome membrane (see, e.g., *PNAS* 84:7851 (1987); *Biochemistry* 28:908 (1989)). When liposomes are endocytosed by a target cell, for example, they become destabilized and release their contents. This destabilization is termed fusogenesis. Dioleoylphosphatidylethanolamine (DOPE) is the basis of many "fusogenic" systems.

Such liposomes typically comprise an ADNF polypeptide and a lipid component, e.g., a neutral and/or cationic lipid, optionally including a receptor-recognition molecule such as an antibody that binds to a predetermined cell surface receptor or ligand (e.g., an antigen). A variety of methods are available for preparing liposomes as described in, e.g., Szoka et al., *Ann. Rev. Biophys. Bioeng.* 9:467 (1980), U.S. Pat. Nos. 4,186,183, 4,217,344, 4,235,871, 4,261,975, 4,485,054, 4,501,728, 4,774,085, 4,837,028, 4,235,871, 4,261,975, 4,485,054, 4,501,728, 4,774,085, 4,837,028, 4,946,787, PCT Publication No. WO 91\17424, Deamer & Bangham, *Biochim. Biophys. Acta* 443:629-634 (1976); Fraley, et al., *PNAS* 76:3348-3352 (1979); Hope et al., *Biochim. Biophys. Acta* 812:55-65 (1985); Mayer et al., *Biochim. Biophys. Acta* 858: 161-168 (1986); Williams et al., *PNAS* 85:242-246 (1988); *Liposomes* (Ostro (ed.), 1983, Chapter 1); Hope et al., *Chem. Phys. Lip.* 40:89 (1986); Gregoriadis, *Liposome Technology* (1984) and Lasic, *Liposomes: from Physics to Applications* (1993)). Suitable methods include, for example, sonication, extrusion, high pressure/homogenization, microfluidization, detergent dialysis, calcium-induced fusion of small liposome vesicles and ether-fusion methods, all of which are well known in the art.

In certain embodiments of the present invention, it is desirable to target the liposomes of the invention using targeting moieties that are specific to a particular cell type, tissue, and the like. Targeting of liposomes using a variety of targeting moieties (e.g., ligands, receptors, and monoclonal antibodies) has been previously described (see, e.g., U.S. Pat. Nos. 4,957, 773 and 4,603,044). Standard methods for coupling targeting agents to liposomes can be used. These methods generally involve incorporation into liposomes lipid components, e.g., phosphatidylethanolamine, which can be activated for attachment of targeting agents, or derivatized lipophilic compounds, such as lipid derivatized bleomycin. Antibody targeted liposomes can be constructed using, for instance, liposomes which incorporate protein A (see Renneisen et al., *J. Biol. Chem.*, 265:16337-16342 (1990) and Leonetti et al., *PNAS* 87:2448-2451 (1990).

Furthermore, the ADNF I and ADNF III polypeptides of the present invention can be embodied in pharmaceutical compositions intended for parenteral, topical, oral or local administration. Preferably, the pharmaceutical compositions are administered parenterally, e.g., intravenously, subcutaneously, intradermally, or intramuscularly, or intranasally. Thus, the invention provides compositions for parenteral administration that comprise a solution of a mixture of ADNF I and ADNF III polypeptides, as described above, dissolved or suspended in an acceptable carrier, preferably an aqueous carrier. A variety of aqueous carriers may be used including, for example, water, buffered water, 0.4% saline, 0.3% glycine, hyaluronic acid and the like. These compositions may be sterilized by conventional, well known sterilization techniques or, they may be sterile filtered. The resulting aqueous solutions may be packaged for use as is or lyophilized, the lyophilized preparation being combined with a sterile solution prior to administration. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride, potassium chloride, calcium chloride, sorbitan monolaurate, triethanolamine oleate, etc.

For solid compositions, conventional nontoxic solid carriers may be used that include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient and more preferably at a concentration of 25%-75%.

For aerosol administration, a mixture of ADNF I and ADNF III polypeptides are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery.

In therapeutic applications, a mixture of ADNF I and ADNF III polypeptides of the invention are administered to a patient in an amount sufficient to prevent neuronal cell death or to reduce a condition associated with fetal alcohol syndrome. An amount adequate to accomplish this is defined as "therapeutically effective dose." Amounts effective for this use will depend on, for example, the particular ADNF I or ADNF III polypeptide employed, the type of neuronal cell death or damage to be prevented, the manner of administration, the weight and general state of health of the patient, and the judgment of the prescribing physician. For example, for the prevention of neuronal cell death, an amount of ADNF I or ADNF III polypeptides falling within the range of a 1 µg to 50 µg, preferably 1 µg to 10 µg dose given intranasally once a day per mouse (e.g., in the evening) would be a therapeutically effective amount. This dose is based on the average body weight of a mouse. Therefore, an appropriate dose can be extrapolated for a human body.

Alternatively, nucleic acids encoding ADNF can also be used to provide a therapeutic dose of ADNF polypeptides. These nucleic acids can be inserted into any of a number of well-known vectors for the transfection of target cells and organisms. For example, nucleic acids are delivered as DNA plasmids, naked nucleic acid, and nucleic acid complexed with a delivery vehicle such as a liposome. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology Doerfler and Böhm* (eds) (1995); and Yu et al., *Gene Therapy* 1:13-26 (1994).

Methods of non-viral delivery of nucleic acids include lipofection, microinjection, biolistics, virosomes, liposomes, immunoliposomes, polycation or lipid:nucleic acid conjugates, naked DNA, artificial virions, and agent-enhanced uptake of DNA. Lipofection is described in, e.g., U.S. Pat. No. 5,049,386, U.S. Pat. No. 4,946,787; and U.S. Pat. No. 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91/17424, WO 91/16024. Delivery can be to cells (ex vivo administration) or target tissues (in vivo administration).

V. Methods for Production of ADNF Polypeptides

A. Recombinant Methods for Production of ADNF Polypeptides

1. Cloning and Isolation of ADNF Nucleic Acids

Several specific nucleic acids encoding ADNF polypeptides are described herein. See, also, e.g., Brenneman & Gozes, *J. Clin. Invest.* 97:2299-2307 (1996), Brenneman, *J. Pharm. Exp. Ther.* 285:619-627 (1998), and Bassan et al., *J. Neurochem* 72:1283-1293 (1999), the teachings of which are hereby incorporated in their entirety by reference. These nucleic acids can be made using standard recombinant or synthetic techniques. Given the nucleic acids of the present invention, one of skill can construct a variety of clones containing functionally equivalent nucleic acids, such as nucleic acids that encode the same ADNF polypeptides. Cloning methodologies to accomplish these ends, and sequencing methods to verify the sequence of nucleic acids are well known in the art. Examples of appropriate cloning and sequencing techniques, and instructions sufficient to direct persons of skill through many cloning exercises are found in Sambrook et al., *Molecular Cloning—A Laboratory Manual* (2nd ed. 1989) and *Current Protocols in Molecular Biology* (Ausubel et al., eds., 1994).

In addition, product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen (San Diego, Calif.), and Applied Biosystems (Foster City, Calif.), as well as many other commercial sources known to one of skill.

The nucleic acid compositions of this invention, whether RNA, cDNA, genomic DNA or a hybrid of the various mixtures, are isolated from biological sources, such as astrocyte, neuroblastoma cells, or fibroblasts, or synthesized in vitro.

The nucleic acids of the invention are present in transformed or transfected cells, in transformed or transfected cell lysates, or in a partially purified or substantially pure form.

In vitro amplification techniques suitable for amplifying sequences for use as molecular probes or generating nucleic acid fragments for subsequent subcloning are known. Examples of techniques sufficient to direct persons of skill through such in vitro amplification methods, including the polymerase chain reaction (PCR), the ligase chain reaction (LCR), Qβ-replicase amplification and other RNA polymerase mediated techniques (e.g., NASBA), are found in Berger, Sambrook et al. and Ausubel et al., all supra, as well as in U.S. Pat. No. 4,683,202; *PCR Protocols A Guide to Methods and Applications* (Innis et al., eds., 1990); Arnheim & Levinson (Oct. 1, 1990) *C&EN* 36-47; *The Journal Of NIH Research* 3:81-94 (1991); Kwoh et al., *Proc. Natl. Acad. Sci. USA* 86:1173 (1989); Guatelli et al., *Proc. Natl. Acad. Sci. USA* 87:1874 (1990); Lomell et al., *J. Clin. Chem* 35:1826 (1989); Landegren et al., *Science* 241:1077-1080 (1988); Van Brunt, *Biotechnology* 8:291-294 (1990); Wu & Wallace, *Gene* 4:560 (1989); Barringer et al., *Gene* 89:117 (1990); and Sooknanan & Malek, *Biotechnology* 13:563-564 (1995). Improved methods of cloning in vitro amplified nucleic acids are described in U.S. Pat. No. 5,426,039. Improved methods of amplifying large nucleic acids are summarized in Cheng et al., *Nature* 369:684-685 (1994) and the references cited therein. One of skill will appreciate that essentially any RNA can be converted into a double stranded DNA suitable for restriction digestion, PCR expansion and sequencing using reverse transcriptase and a polymerase.

Oligonucleotides for use as probes, for example, with in vitro ADNF nucleic acid amplification methods, or for use as nucleic acid probes to detect ADNF nucleic acids, are typically synthesized chemically according to the solid phase phosphoramidite triester method described by Beaucage & Caruthers, *Tetrahedron Letts.* 22(20):1859-1862 (1981), e.g., using an automated synthesizer, e.g., as described in Needham-VanDevanter et al., *Nucleic Acids Res.* 12:6159-6168 (1984). Oligonucleotides can also be custom made and ordered from a variety of commercial sources known to those of skill in the art. Purification of oligonucleotides, where necessary, is typically performed by either native acrylamide gel electrophoresis, or by anion-exchange HPLC as described in Pearson & Regnier, *J. Chrom.* 255:137-149 (1983). The sequence of the synthetic oligonucleotides can be verified using the chemical degradation method of Maxam & Gilbert, in *Methods in Enzymology* 65:499-560 (Grossman & Moldave, eds., 1980).

One of skill will recognize many ways of generating alterations in a given nucleic acid sequence. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques (see, Giliman & Smith, *Gene* 8:81-97 (1979); Roberts et al., *Nature* 328:731-734 (1987); and Sambrook et al., *Molecular Cloning—A Laboratory Manual* (2nd ed. 1989)).

2. Recombinant Expression of ADNF Polypeptides

In one embodiment, the polypeptides, or subsequences thereof, are synthesized using recombinant nucleic acid methodology. Generally, this involves creating a nucleic acid sequence that encodes the protein, placing the nucleic acid in an expression cassette under the control of a particular promoter, expressing the protein in a host cell, isolating the expressed protein and, if required, renaturing the protein.

Once a nucleic acid encoding an ADNF polypeptide of the invention is isolated and cloned, the nucleic acid is optionally expressed in recombinantly engineered cells known to those of skill in the art. Examples of such cells include, but are not limited to, bacteria, yeast, plant, filamentous fungi, insect (especially employing baculoviral vectors) and mammalian cells. The recombinant nucleic acids are operably linked to appropriate control sequences for expression in the selected host. For *E. coli*, example control sequences include the T7, trp, or lambda promoters, a ribosome binding site and, preferably, a transcription termination signal. For eukaryotic cells, the control sequences typically include a promoter and, preferably, an enhancer derived from immunoglobulin genes, SV40, cytomegalovirus, etc., and a polyadenylation sequence, and may include splice donor and acceptor sequences.

If desired, recombinant nucleic acids can be constructed to encode a fusion polypeptide comprising an ADNF polypeptide. For example, a nucleic acid encoding an ADNF I polypeptide can be linked to a nucleic acid encoding an ADNF III polypeptide to provide a mixture of ADNF polypeptides. In another example, a nucleic acid encoding an ADNF polypeptide (e.g., an ADNF I polypeptide, an ADNF III polypeptide, or a fusion ADNF I/ADNF III polypeptide) can be linked with another nucleic acid, such as a portion of HIV tat nucleic acid, which facilitates the delivery of the ADNF III polypeptide into tissues. In yet another example, a nucleic acid encoding an ADNF polypeptide can be linked to nucleic acids that encode affinity tags to facilitate protein purification protocol. An ADNF nucleic acid and a heterologous polynucleotide sequence can be modified to facilitate their fusion and subsequent expression of fusion polypeptides. For example, the 3' stop codon of the ADNF polynucleotide sequence can be substituted with an in frame linker sequence, which may provide restriction sites and/or cleavage sites.

The plasmids of the invention can be transferred into the chosen host cell by well-known methods. Such methods include, for example, the calcium chloride transformation method for *E. coli* and the calcium phosphate treatment or electroporation methods for mammalian cells. Cells transformed by the plasmids can be selected by resistance to antibiotics conferred by genes contained on the plasmids, such as the amp, gpt, neo, and hyg genes.

Once expressed, the recombinant ADNF polypeptides or naturally occurring can be purified according to standard procedures of the art, including ammonium sulfate precipitation, affinity columns, column chromatography, gel electrophoresis and the like (see, e.g., Scopes, *Polypeptide Purification* (1982); Deutscher, *Methods in Enzymology Vol. 182: Guide to Polypeptide Purification* (1990)). Once purified, partially or to homogeneity as desired, the ADNF polypeptides may then be used, e.g., to prevent neuronal cell death or to treat a condition associated with fetal alcohol syndrome. See, also, e.g., Brenneman & Gozes, *J. Clin. Invest.* 97:2299-2307 (1996), Brenneman et al., *J. Pharm. Exp. Ther.* 285:619-627 (1998), and Bassan et al. *J. Neurochem* 72:1283-1293 (1999), the teachings of which are hereby incorporated in their entirety by reference B. Synthesis of ADNF Polypeptides In addition to the foregoing recombinant techniques, the ADNF polypeptides of the invention are optionally synthetically prepared via a wide variety of well-known techniques. Polypeptides of relatively short size are typically synthesized in solution or on a solid support in accordance with conventional techniques (see, e.g., Merrifield, *Am. Chem. Soc.* 85:2149-2154 (1963)). Various automatic synthesizers and sequencers are commercially available and can be used in accordance with known protocols (see, e.g., Stewart & Young, *Solid Phase Peptide Synthesis* (2nd ed. 1984)). Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany & Merrifield, *Solid-Phase Peptide Synthesis*; pp. 3-284 in *The Peptides Analysis, Synthesis, Biology. Vol. 2: Special Methods in Peptide Synthesis, Part A.*; Merrifield et al., *J. Am. Chem. Soc.* 85:2149-2156 (1963); and Stewart et al., *Solid Phase Peptide Synthesis* (2nd ed. 1984).

After chemical synthesis, biological expression or purification, the polypeptide(s) may possess a conformation substantially different than the native conformations of the constituent polypeptides. In this case, it is helpful to denature and reduce the polypeptide and then to cause the polypeptide to re-fold into the preferred conformation. Methods of reducing and denaturing polypeptides and inducing re-folding are well known to those of skill in the art (see Debinski et al., *J. Biol. Chem.* 268:14065-14070 (1993); Kreitman & Pastan, *Bioconjug. Chem.* 4:581-585 (1993); and Buchner et al., *Anal. Biochem.* 205:263-270 (1992)). Debinski et al., for example, describe the denaturation and reduction of inclusion body polypeptides in guanidine-DTE. The polypeptide is then refolded in a redox buffer containing oxidized glutathione and L-arginine.

One of skill will recognize that modifications can be made to the polypeptides without diminishing their biological activity. Some modifications may be made to facilitate the cloning, expression, or incorporation of the targeting molecule into a fusion polypeptide. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

C. Conservative Modifications of the ADNF Nucleic Acids and Polypeptides

One of skill will appreciate that many conservative variations of the ADNF nucleic acid and polypeptide sequences provided herein yield functionally identical products. For example, due to the degeneracy of the genetic code, "silent substitutions" (i.e., substitutions of a nucleic acid sequence that do not result in an alteration in an encoded polypeptide) are an implied feature of every nucleic acid sequence that encodes an amino acid. Similarly, "conservative amino acid substitutions," in one or a few amino acids in an amino acid sequence are substituted with different amino acids with highly similar properties (see the definitions section, supra), are also readily identified as being highly similar to a disclosed amino acid sequence, or to a disclosed nucleic acid sequence that encodes an amino acid. Such conservatively substituted variations of each explicitly listed nucleic acid and amino acid sequences are a feature of the present invention.

One of skill will recognize many ways of generating alterations in a given nucleic acid sequence. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques (see Giliman & Smith, *Gene* 8:81-97 (1979); Roberts et al., *Nature* 328:731-734 (1987)). For example, alanine scanning can be used to determine conservatively modified variants for SALLRSIPA (SEQ ID NO:1) or NAPVSIPQ (SEQ ID NO:2) (i.e., by substituting each amino acid one by one with an alanine or other small neutral amino acid and assay for activity as described herein).

Polypeptide sequences can also be altered by changing the corresponding nucleic acid sequence and expressing the polypeptide. Polypeptide sequences are also optionally generated synthetically using commercially available peptide synthesizers to produce any desired polypeptide (see, Merrifield, supra, and Stewart & Young, supra).

More particularly, it will be readily apparent to those of ordinary skill in the art that the ADNF polypeptides of the present invention can readily be screened for neuroprotective/neurotrophic activity by employing the following CNS assay. Cerebral cortical cell cultures are prepared using the techniques described by Forsythe & Westbrook, *J. Physiol. Lond.* 396:515 (1988) with the following modifications. Cerebral cortex are used instead of hippocampus, and newborn rats are used instead of E16 mice. After nine days growth in vitro, the cultures are given a complete change of medium and treated with the ADNF polypeptide of interest (dissolved in phosphate buffered saline) for an additional five days. To terminate, the cells are fixed for immunocytochemistry and neurons identified with antibodies against NSE (i.e., neuron specific enolase, a neuronal specific marker). Cell counts are performed on 30 fields, with total area of about 15 $mm^2$. Neurons are counted without knowledge of treatment. Control counts not treated with any drugs should run for purposes of comparison. Furthermore, assays described by, e.g., Hill et al., *Brain Res.* 603:222-233 (1993); Venner & Gupta., *Nucleic Acid Res.* 18:5309 (1990); and Peralta et al., *Nucleic Acid Res.* 18:7162 (1990) can be used.

Using these assays, one of ordinary skill in the art can readily prepare a large number of ADNF polypeptides in accordance with the teachings of the present invention and, in turn, screen them using the foregoing assay to find ADNF polypeptides, in addition to those set forth herein, which possess the neuroprotective/neurotrophic activity of the intact ADNF growth factor. For instance, using ADNF III-8 (i.e., Asn-Ala-Pro-Val-Ser-Ile-Pro-Gln; SEQ ID NO:2) as a starting point, one can systematically add, for example, Gly-, Gly-Gly-, Leu-Gly-Gly- to the N-terminus of ADNF III-8 and, in turn, screen each of these ADNF III polypeptides in the foregoing assay to determine whether they possess neuroprotective/neurotrophic activity. In doing so, it will be found that additional amino acids can be added to both the N-terminus and the C-terminus of the newly discovered active site, i.e., Asn-Ala-Pro-Val-Ser-Ile-Pro-Gln (SEQ ID NO:2), without loss of biological activity as evidenced by the fact that the intact ADNF III growth factor exhibits extraordinary biological activity. This discussion also applies to ADNF I polypeptides.

EXAMPLES

I. Materials and Methods

A. Animals

C57-B16J female mice (Jackson Labs) were kept under a 12 h light, 12 h dark regimen with food and water available at all times. The mice received humane animal care in compliance with the "Guideline for Care, and Use of Experimental Animals." Six week old females (21-24 grams) were mated with C57-B16J males for 4 h. The presence of a vaginal plug was considered day 0 pregnancy.

B. Treatment Groups

A published well-delineated model for FAS was followed (Webster et al., *Neurobehav Tox,* 2:227-34 (1980)). Animals were injected (intraperitoneal) on E8 with 25% ethyl alcohol in saline (v/v) or vehicle alone at 0.030 ml/g body weight at 0900 on E8. Pretreatment with VIP and ADNF polypeptides (e.g., NAP, SAL, NAP+SAL) were given 30 min prior to alcohol. Post-treatment with NAP+SAL was given at 1 or 3 h after alcohol. Dosages of the neuropeptides were NAP (20 μg and 40 μg), SAL (20 μg), NAP (20 μg)+SAL (20 μg); VIP (1 μg). NAP+SAL without alcohol was also studied. NAP was diluted in 50 μl DMSO and diluted in filtered Dulbecco's phosphate buffered saline (DPBS). SAL was dissolved and diluted in filtered DPBS. VIP was dissolved in 20 μl glacial acetic acid and diluted in HPLC water and DPBS. Since the animals receiving alcohol were incapacitated for approximately 6 hours following injection, food and water were withheld from all groups for the initial 6 hours, to allow accurate assessment of fetal weights.

C. Morris Water Maze Test

Pregnant mice were treated on embryonic day 8 with vehicle alone (control), alcohol (intraperitoneal injection of 25% ethanol v/v at 0.03 ml/kg), pretreatment with NAP+SAL (intraperitoneal) 30 minutes before alcohol. The animals were allowed to deliver naturally (housed 2 mice of same treatment per cage). Weaning occurred on day 20, at which time the male offspring were eartagged, removing all traces of their treatment group. Only male mice were used for the watermaze trials. Testing of mice began at 35-50 days, twice daily (two trials) for 7 days.

Morris water maze test used is adapted from "Repeated acquisition of a spatial navigation task in mice: Effects of spacing of trials and of unilateral middle cerebral artery occlusion" Klapdor & Van der Staay, *Physiology & Behav.* 63(5):903-909 (1998). A trial consists of attempting to find the hidden platform from 4 set points. Specifically, testing of mice began in the mornings, typically between 9 and 9:30. Consistent timing is important to any behavioral study. Testing of mice was performed in a random order to prevent chronological bias by the researcher. Maze is set up the day before, to allow water time to adjust to room temperature. 100-150 ml of non-toxic white tempura is added and mixed. Before beginning each day, water is agitated to homogenize paint, and additional water is added to assure that a consistent water level of 7-10 ml above the platform is maintained despite evaporation. The software is set up so that the masking is optimal, and each of two trials is timed at 60 seconds. The active platform is set for the number 1 quadrant.

Mice are allowed to sit on the platform for 1 minute on Day 1, in order to acclimate to their surroundings and gain an initial sense of where the escape platform is located. It is normal for the mice to jump off the platform and swim around in exploration at this initial stage. This should be permitted briefly, but the mice should be returned to the platform after a few seconds of swimming is completed.

Mice are released into the maze from the midline separating quadrants 2 and 3 (west), facing the outside of the maze. They are allowed to swim for 60 seconds, or until they reach the platform on their own. If they are unsuccessful in finding the platform, they are manually returned to it. All mice are allowed to remain on the platform for 15 seconds after their first trial.

The second trial is then administered in the same manner as the first (same release position, same platform position, etc.), again allowing the mice 15 seconds on the platform before returning them to their drying cages (equipped with chix wipe to absorb extra water).

On days 2-7, mice are only given 15 seconds on the platform before the initial trial. This is enough for them to become adjusted to the water temperature. Their propensity to flee the platform during this stage exhibits a remarkable declination from day one, as most mice will stay without attempting to leave the platform.

Mice should be returned to their normal cages after allowing 5-10 minutes for them to become dry. The daily average escape latency is calculated and plotted along the 7 day period for test administration.

Many mice exhibiting decreased spatial learning and memory will display behavioral anomalies, including thigmotaxis (wall hugging) and floating. This has been documented by Minichiello et al., *Neuron* 24(2):401-414 (1999).

The average of the two trials was taken and used for statistical analysis. There were 9 alcohol pups, 15 control and 15 NAP+SAL+alcohol pups. Statistical analysis was with ANOVA with Bonferroni correction for multiple analyses (overall $P<0.007$ considered significant) and Fisher's post hoc for determination of significantly different pairs.

D. Evaluation of Fetal Weights/Litters

At E18 (embryonic gestation day 18), the number of live and demised fetuses was determined. Fetal weights and fetal brain weights were obtained for each fetus in the litter. The mean fetal weights were determined for each mother, and this was used for statistical analysis.

E. mRNA and Protein Determination

At 6, 24 and 48 h after treatment (days 8, 9, and 10), conceptuses were explanted from the uterus within decidua (embryo, membranes, trophoblast, decidua, and fluid) and a piece of maternal cerebral cortex was removed from at least three different pregnant mice. Treatment groups were alcohol, control, and NAP+SAL+alcohol with the NAP+SAL given 30 min before alcohol. At least three samples were examined per group, in addition, embryo/decidual samples were pooled in groups of three. These samples were frozen on dry ice, and stored at −80° C. until analyzed for VIP levels. VIP levels in embryo/decidua and maternal cortex were performed at 6, 24, and 48 h after treatment using enzyme linked immunosorbant assay (ELISA, Peninsula laboratories, Belmont, Calif.) as previously described (see, Spong et al., *Endocrinol.* 140:917 (1999)). The linear range of the ELISA for VIP is 0.04-2.0 ng/ml. Concentrations of VIP were calculated per mg protein. Detection limit of the ELISA was 0.5 ng/10 μg protein. Other samples were homogenized as previously described for mRNA quantitation (Spong et al. (1999), supra). Quantitation of VIP mRNA was performed with mimic cDNA primers as previously described Spong et al. (1999), supra). The crossover values, when the mimic cDNA crossed to product cDNA, from the treatment groups were compared to those from control groups.

F. VIP Binding

In vitro autoradiography with $^{125}$I-VIP was performed on 20 μm cryostat sections of pregnant uteri, 6, 24 and 48 h after treatment with control, alcohol or NAP+SAL+alcohol as previously described (Dibbern et al., *J Clin Invest* 99:2837-41 (1997)). The density of labeled VIP binding was analyzed by digitizing the film images using a Macintosh II-based image analysis system (IMAGE, Wane Rasband, Research Services Brance, NIMH). Density measurements were taken from 2 or more images, from each of 3 or more uteri. The specific binding was determined by subtracting the light transmittance from brain sections incubated with $10^{-6}$ M unlabeled VIP from total light transmittance.

G. Statistics

The mean litter pup and fetal brain weight was calculated, with the litter mean used for all statistical analysis. Percent demises were calculated by dividing the number of demises by the total number of fetuses (live plus demises). Statistical analysis included ANOVA for continuous variables, Mann-Whitney U for nonparametric data, Chi square for categorical variables or Fisher's exact test where appropriate [Statview 4.5 (Abacus Concepts, Inc., Berkeley, Calif.)] with p<0.05 considered significant. Results are presented as mean±standard error unless specified.

II. RESULTS

The C57B1/6J mouse strain provided a well-characterized model for FAS. Previous work with this strain has defined the effects of dosage and embryonic timing on maternal serum alcohol levels and embryonic effects (Webster et al., *Neurobehav Tox,* 2:227-34 (1980)), incorporated herein by reference. Since treatment on E8 resulted in the highest rate of fetal anomalies and demises (Webster et al. (1980), supra), and VIP's growth regulating effects on the embryo are limited to the early post-implantation period, E8 was chosen as the optimal and most severe test for the protective activity of the neuropeptides. For accurate replicability of alcohol and peptide administration we chose a model utilizing intraperitoneal injection (Webster et al., (1980), supra). This model replicates many of the features of FAS including alcohol-induced fetal malformations and death. The highest alcohol dose in the model (Webster et al., (1980), supra) was chosen for the most severe test of efficacy. Although the intraperitoneal model results in higher blood alcohol concentrations than an oral route, we were assured of similar alcohol levels in the groups as previously measured (Webster et al., (1980), supra) and a stringent test to evaluate treatment efficacy.

Treatment groups included: alcohol alone, to confirm the model; control to confirm that the dilutant/injection was not deleterious; pretreatment with NAP (20 μg) or SAL (20 μg) to evaluate their efficacy in preventing FAS; pretreatment with VIP (1 μg); combination pretreatment with NAP (20 μg)+ SAL (20 μg) to evaluate if the mixture of the two peptides is more efficacious in preventing FAS; pretreatment with NAP (40 μg) to determine if the efficacy seen with the mixture of NAP+SAL pretreatment is due to the increased dosage or an effect of the two different peptides; treatment with NAP (20 μg)+SAL (20 μg) without alcohol to evaluate for toxicity of the peptides without the stress of alcohol.

A. Assessment of Learning Using Morris Watermaze Test

Assessment of learning utilized the Morris watermaze as described in the Materials and Methods Section. Adult male offspring from treated litters (30-55 days of life) were tested twice daily for 7 days. Males from the alcohol-treated litters did not learn over the seven day period (FIG. 1) in contrast to those from the control litters, who decreased their latency to find the hidden platform by 50% (P<0.001). Males from the litters who were pre-treated with NAP+SAL and then given alcohol also significantly learned (P≦0.001), with a learning curve similar to control.

B. Fetal Death

Figure 2:
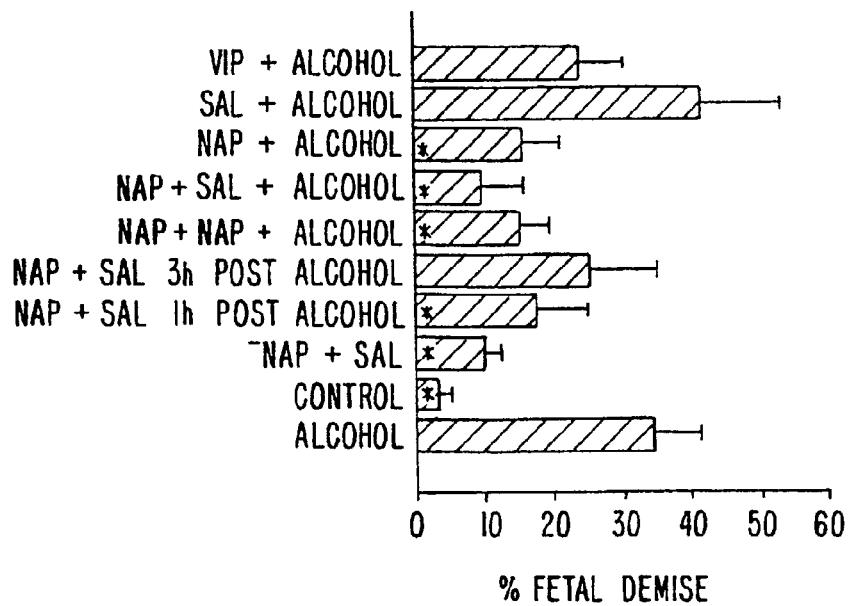
FIG. 2 illustrates that pretreatment with NAP+SAL increased fetal viability in fetuses exposed to alcohol. At E18, the number of living and demised embryos was counted and the % of demises calculated. Comparisons are made to the alcohol group, overall ANOVA p<0.001. Post hoc Fishers tests were performed, with the * groups significantly different than alcohol (all post-hoc p<0.03). [The litter size (living+demises) was not different between the groups, with an average litter size of 8 fetuses]. The number of fetuses per treatment groups ranged between 120 and 280. The litter mean was used for analysis. The number of litters in each group were: control (34), alcohol (40), NAP+alcohol (25), NAP+NAP+alcohol, a double dose of NAP (17), SAL+alcohol (15), VIP+alcohol (18), NAP+SAL+alcohol (20), NAP+SAL alone (19), NAP+SAL 1 h post alcohol (18), NAP+SAL 3 h post alcohol (14). Statistical analysis included ANOVA for continuous variables, Mann-Whitney U for nonparametric data, Fisher's exact test for categorical variables [Statview 4.5 (Abacus Concepts, Inc., Berkeley, Calif.)] with p<0.05 considered significant.

The number of fetal demises was determined to assess the protective effects of the ADNF polypeptides. The percentage of fetal demises was significantly higher in the alcohol than control group. Pretreatment with NAP or the mixture of NAP+SAL, or post-treatment at 1 h with NAP+SAL prevented the death seen with alcohol (each P<0.05, FIG. 2). Pretreatment with VIP did not reverse the fetal death rate (FIG. 2). Treatment with NAP+SAL without alcohol exposure did not affect the rate of fetal death (FIG. 2).

C. Fetal Weights and Fetal Brain Weights

Figure 3A:
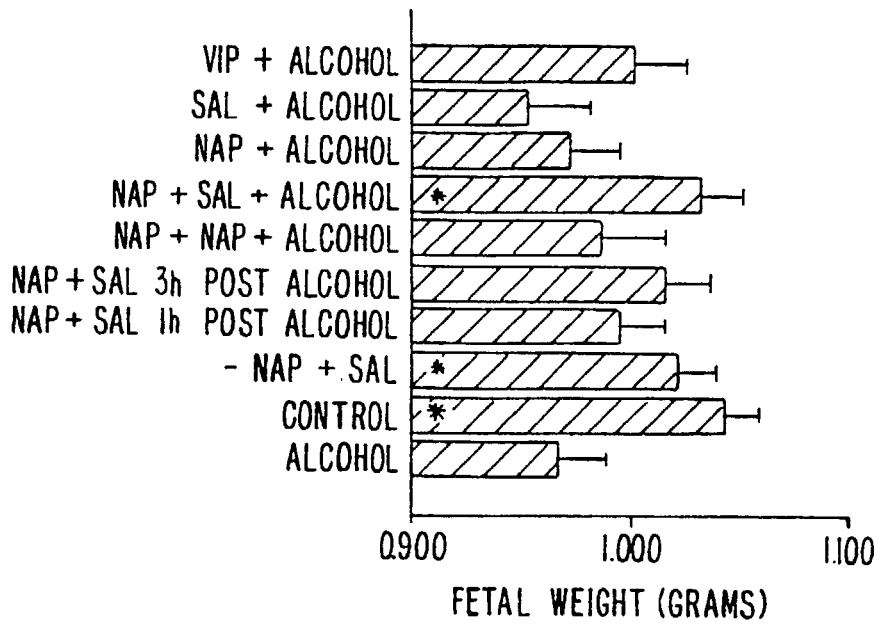
FIG. 3a and FIG. 3b illustrate that NAP+SAL prevented fetal growth restriction and microcephaly. Fetal weights (FIG. 3a) and brain weights (FIG. 3b) for each pregnant female were obtained at E18. Pretreatment with NAP+SAL prevented the growth restrictions associated with alcohol. Post-treatment at 1 and 3 h with NAP+SAL prevented the microcephaly associated with alcohol. Comparisons are made to the alcohol group, and overall ANOVA is p<0.001. Post hoc Fishers tests were performed, with the * groups significantly different than alcohol. The mean from each litter was used for statistical analysis. Average litter size was 8-10 fetuses; thus, there were approximately 110-330 fetuses in each group. Sample sizes were control (33), alcohol (32), NAP+alcohol (24), NAP+NAP+alcohol (17), SAL+alcohol (11), VIP+alcohol (17), NAP+SAL+alcohol (19), NAP+SAL alone (19), NAP+SAL 1 h post alcohol (17), NAP+SAL 3 h post alcohol (11).
Figure 3B:
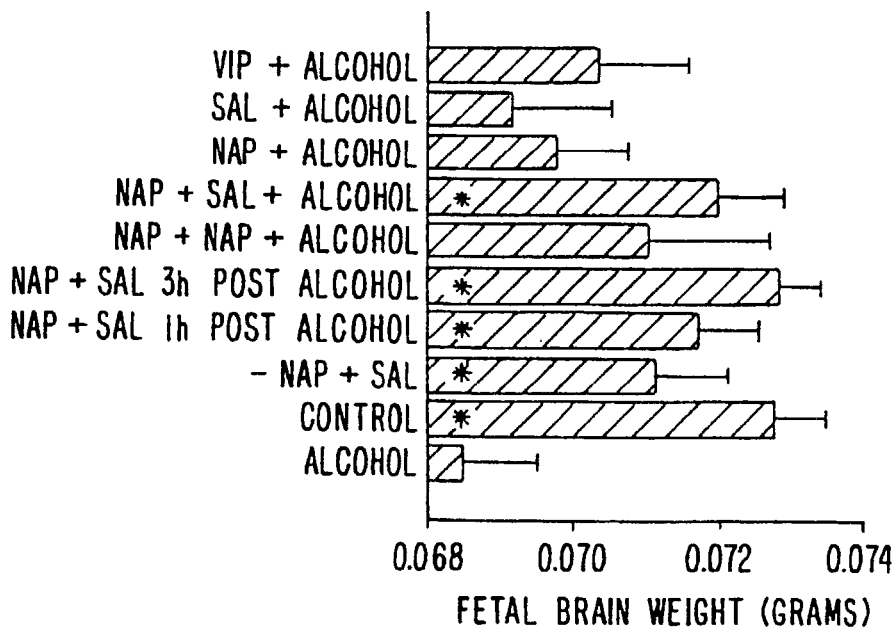

In the surviving E18 fetuses, fetal and fetal brain weights were evaluated to assess the protective effects of the ADNF polypeptides. Both fetal weights and fetal brain weights were significantly smaller in the alcohol treated group than in control or those pretreated with NAP+SAL (FIGS. 3a, 3b). Pretreatment with NAP alone moderately prevented the alcohol-induced growth restrictions. Pretreatment with SAL alone did not prevent the alcohol-induced fetal weight reduction, but moderately prevented the alcohol-induced fetal brain weight reduction. Similarly, pretreatment with a double dosage of NAP (40 μg) moderately prevented the alcohol-induced growth restriction, indicating that it is the mixture of the two ADNF (ADNF I and ADNF III) peptides, rather than the dosage, required for the superior effect shown with a combination of NAP+SAL. Post-treatment with NAP+SAL (1 h and 3 h) prevented the microcephaly, but not the growth restriction. Pretreatment with VIP improved embryonic weights; however, the effect was intermediate and not statistically significant. NAP+SAL treatment without alcohol exposure did not affect fetal weights. (FIGS. 3a, 3b).

D. VIP Levels

Figure 4A:
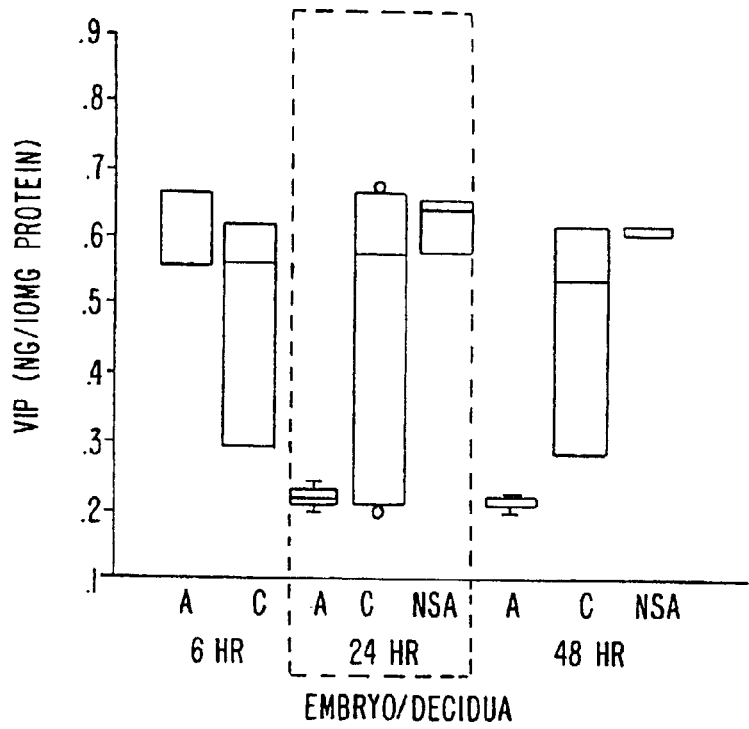
FIG. 4a and FIG. 4b illustrate that NAP+SAL pretreatment prevented decline in VIP levels decline after alcohol treatment. VIP levels in embryo/decidua (FIG. 4a) and maternal cortex (FIG. 4b) were measured with ELISA at 6, 24, and 48 hours after treatment on E8. Treatment groups were alcohol (A), control (C) and NAP+SAL+alcohol (NSA), with the NAP+SAL given 30 minutes before alcohol. At least three samples were run per group, in addition, embryo/decidual samples were pooled in groups of 3. Detection limit of the ELISA was 0.5 ng/10 µg protein and is represented by a line. Box plots are graphed with the median value represented as middle bar, box representing 95% of the data and 99% of data contained within whiskers. Outlying values are graphed as individual points. In the embryo, NAP+SAL pretreatment prevented the alcohol-induced decline in VIP levels at 24 and 48 hours (FIG. 4a). In the maternal cortex, NAP+SAL pretreatment prevented the alcohol-induced decline in VIP levels at 6 and 24 hours (P<0.05). All values were similar in maternal cortex at 48 h.
Figure 4B:
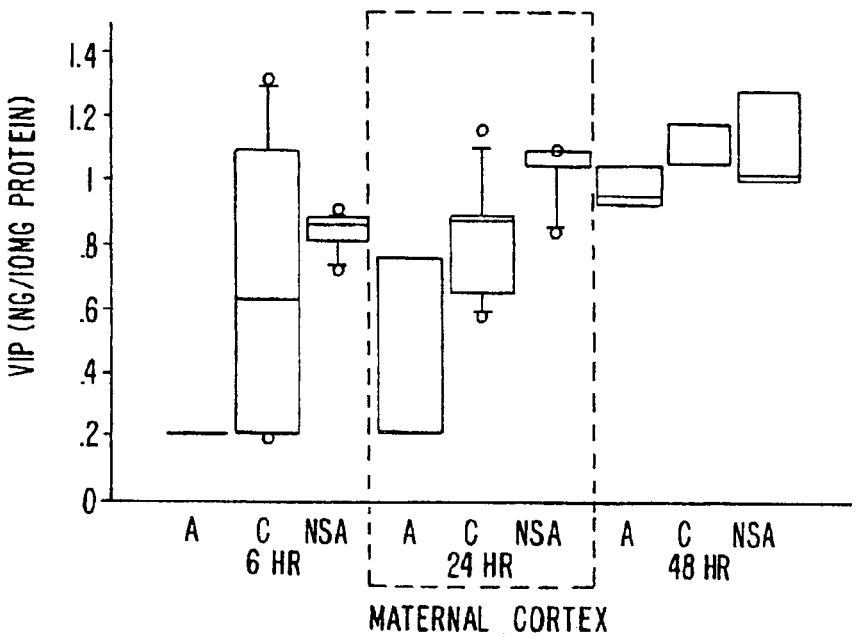

To evaluate the effect of alcohol exposure on VIP, levels were measured in treated embryo/decidua and maternal cortex. NAP+SAL pretreatment prevented the alcohol-induced decline in embryo/decidua VIP levels at 24 and 48 h after treatment (P≦0.001) (FIG. 4a). NAP+SAL pretreatment also prevented the alcohol-induced decline in maternal cortex VIP levels at 6 and 24 h after alcohol. (p<0.001) (FIG. 4b). At 48h, all groups had similar maternal cortex VIP levels. Thus, there appears to be a temporal relationship between maternal alcohol administration and VIP levels, with an initial decline in maternal cortex VIP levels at 6 h and 24 h and recovery by 48 h whereas in the embryo/decidua the levels are not affected until a significant decline at 24-48 h.

Figure 5:
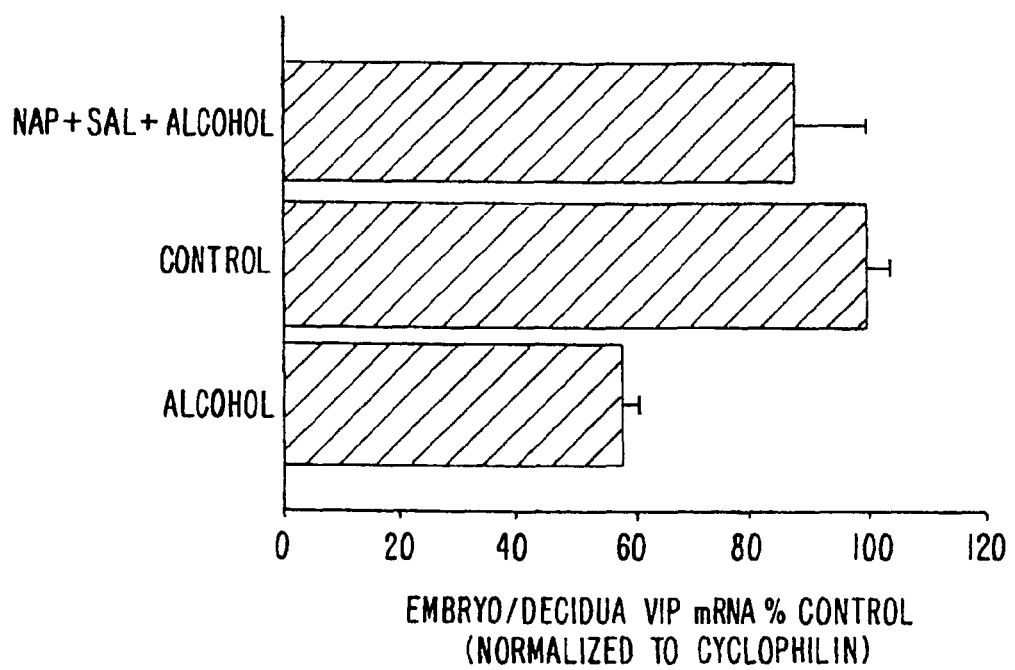
FIG. 5 illustrates the effect of ADNF polypeptides on the VIP mRNA level after alcohol treatment. VIP mRNA was quantitated in embryo/decidua 6 hours after treatment. Treatment groups were alcohol, control and NAP+SAL+alcohol, with the NAP+SAL given 30 min before alcohol. Embryo/decidual samples were pooled in groups of 3, at least three samples were run per treatment. Both VIP and cyclophilin mRNA were quantitated and the VIP mRNA was normalized to cyclophilin and expressed as the percentage of control values. Alcohol treatment significantly decreased VIP mRNA, whereas pretreatment with NAP+SAL brought VIP mRNA levels back to control.

VIP mRNA also has a defined temporal relationship in early pregnancy with a significant increase in the decidua at E6-E8 compared to E17 (Spong et al., (1999), supra). Quantitative rt-PCR of the embryo/decidua demonstrated a significant decline in VIP mRNA levels 6 h after alcohol treatment, to 58% of control levels (p≦0.02). (FIG. 5) However, pretreatment with NAP+SAL increased VIP mRNA levels to those of controls (87%).

VIP binding sites were significantly increased to 25% greater than control in the decidua of the alcohol-treated embryos at 6 h and remained elevated at 24 and 48 h, indicating a long-lasting effect of alcohol-induced changes. Pretreatment with NAP+SAL had no effect on the alcohol-induced upregulation of VIP binding sites.

E. ADNF Polypeptides Prevent Alcohol Induced Decline in GSH/GSSG

In vivo and in vitro studies have shown that a single exposure of ADNF polypeptides can result in long-term effects. In vitro studies have demonstrated that these peptides have oxidative protectant properties as well as effects on cellular transcription. To determine if part of the mechanism of the prevention of alcohol-induced toxicity was related to oxidative stress, glutathione levels (both reduced, GSH, and oxidized, GSSG) were measured in gestations (embryo+decidua) 8 h after treatment (FIG. 6). The conversion of GSH to GSSG is widely recognized as a reliable index of oxidative stress (Halliwell & Gutteridge, *Biochem. J.* 219:1 (1984)). Alcohol treatment resulted in a significant decline of GSH/GSSG to 50% of control (P<0.005). NAP+SAL pretreatment prevented the alcohol-induced decline in GSH/GSSG, with levels comparable to control (90% of control) suggesting that these peptides act, at least in part, as oxidative protectants.

F. Bioavailability of ADNF Polypeptides

Figure 7A:
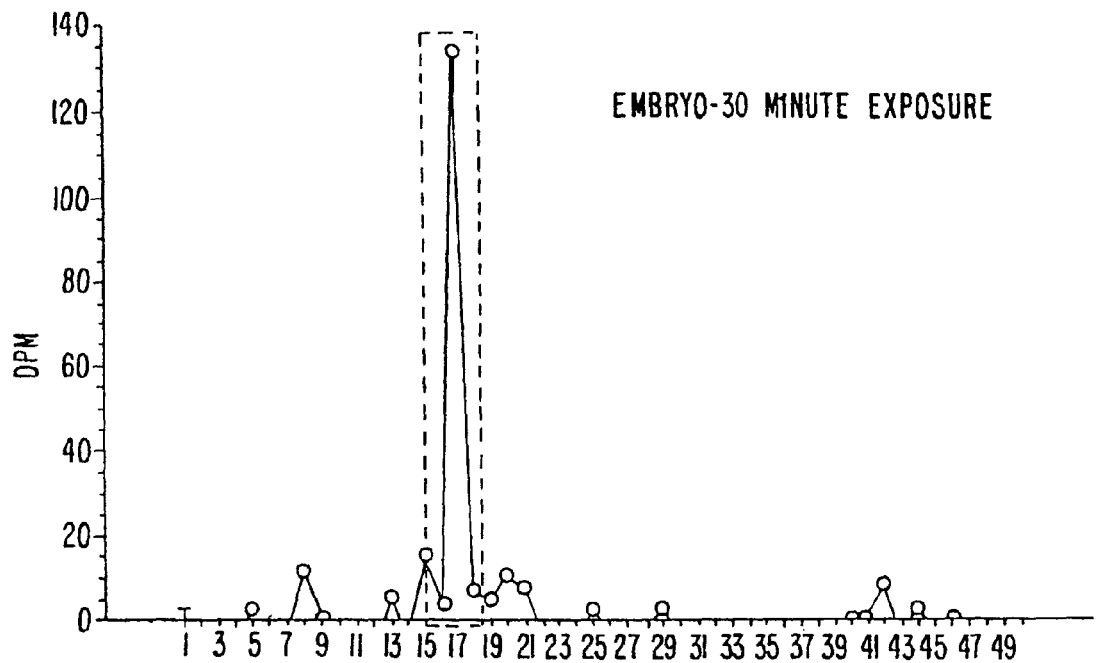
FIG. 7a and FIG. 7b illustrate chromatographs of radiolabel ($^3$H) present in 1 ml fractions from a size exclusion column (Superdex Peptide HR 10/30, Pharmacia Biotech). $^3$H-NAP (2 µCi/20 µg) was administered intraperitoneally to pregnant mice at E8. Intact NAP was present in fractions 15-17 denoted by shaded grey bar on graphs.
Figure 7B:
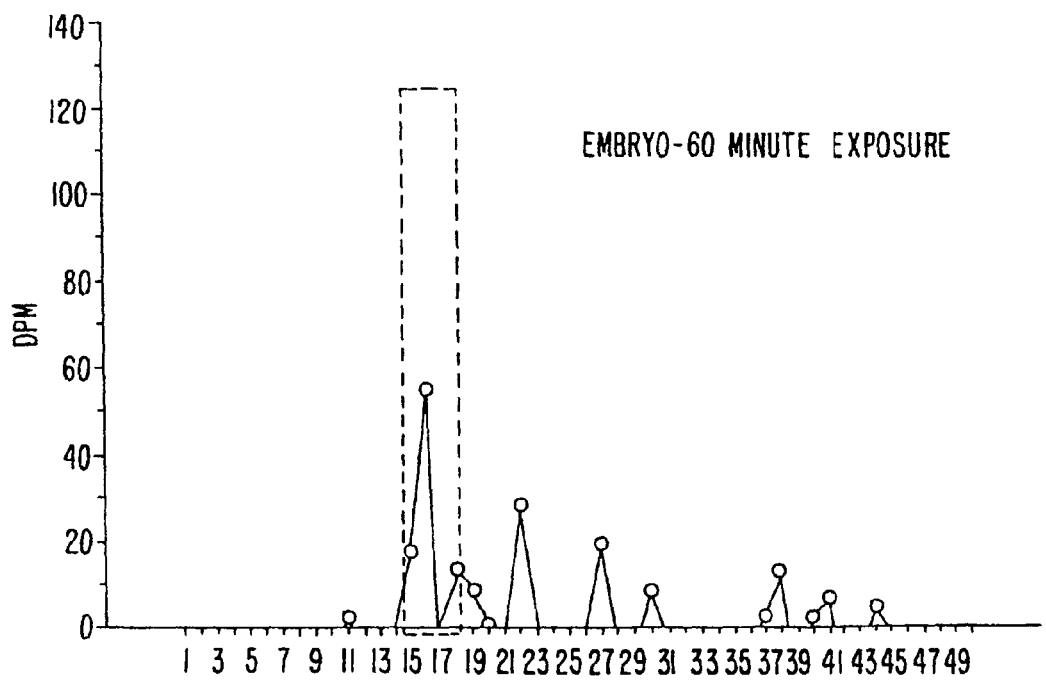

The bioavailability of NAP to embryos was assessed by intraperitoneal administration of $^3$H-NAP (2 μCi/20 μg) to pregnant mice at E8. Chromatographic analysis on a size exclusion column (Superdex Peptide HR 10/30, Pharmacia Biotech) demonstrated that 60% of the radioactivity recovered in the embryo co-migrated with intact NAP 30 min after administration. Based on this accumulation of labeled peptide, approximately 0.2 pmole of NAP was found in the embryo, with an estimated concentration of 10 nM, well within the therapeutic range of NAP. See FIG. 7.

These findings demonstrate that administration of ADNF polypeptides prevents alcohol-induced fetal demise, growth restrictions and learning abnormalities in a model of FAS. Adult male offspring from alcohol-treated litters were unable to learn in the Morris watermaze. However, treatment with ADNF polypeptides in addition to the alcohol prevented this learning deficit. In addition, peptide intervention was successful in the prevention of fetal death, even when given one hour after alcohol administration. Assessment of the protective effects of the peptides in the offspring demonstrated that not only were the acute effects of alcohol toxicity abated, but the long term sequelae was prevented as determined by the prevention of learning abnormalities. The remarkable in vivo stability of these peptides is evident as 60% of labeled NAP was recovered intact in the embryo 30 minutes after administration. Not wishing to be bound by a theory, the mechanism is likely indirect and appears to be in part linked to the embryonic growth regulator VIP, with prevention of alterations in VIP and VIP mRNA levels after alcohol administration as well as via oxidative protection. These findings suggest that ADNF polypeptides, including NAPVSIPQ (SEQ ID NO:2) and SALLRSIPA (SEQ ID NO:1), may also have therapeutic value in treatment of other conditions due to oxidative stress.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. A method for reducing a condition associated with fetal alcohol syndrome in a subject who is exposed to alcohol in utero, the method comprising the steps of:
  (i) selecting a pregnant female having consumed alcohol during pregnancy in an amount sufficient to initiate a condition associated with fetal alcohol syndrome in the subject; and
  (ii) administering to the subject an activity dependent neurotrophic factor (ADNF) polypeptide in an amount sufficient to reduce in the subject the condition associated with fetal alcohol syndrome,
  wherein the ADNF polypeptide is a member selected from the group consisting of:
  (a) an ADNF I polypeptide comprising an active core site having the amino acid sequence Ser-Ala-Leu-Leu-Arg-Ser-Ile-Pro-Ala (SEQ ID NO:1);
  (b) an ADNF III polypeptide comprising an active core site having the amino acid sequence Asn-Ala-Pro-Val-Ser-Ile-Pro-Gln (SEQ ID NO:2); and
  (c) a mixture of the ADNF I polypeptide of (a) and the ADNF III polypeptide of (b).

2. The method of claim 1, wherein the ADNF polypeptide is a member selected from the group consisting of:
  (a) a full length ADNF I polypeptide,
  (b) a full length ADNF III polypeptide, and
  (c) a mixture of a full length ADNF I polypeptide and a full length ADNF III polypeptide.

3. The method of claim 1, wherein the ADNF polypeptide is an ADNF I polypeptide.

4. The method of claim 3, wherein the ADNF I polypeptide consists of the amino acid sequence Ser-Ala-Leu-Leu-Arg-Ser-Ile-Pro-Ala (SEQ ID NO:1).

5. The method of claim 3, wherein the ADNF I polypeptide consists of an amino acid sequence selected from the group consisting of:
  (a) Val-Leu-Gly-Gly-Gly-Ser-Ala-Leu-Leu-Arg-Ser-Ile-Pro-Ala (SEQ ID NO:14);
  (b) Val-Glu-Glu-Gly-Ile-Val-Leu-Gly-Gly-Gly-Ser-Ala-Leu-Leu-Arg-Ser-Ile-Pro-Ala (SEQ ID NO:15);
  (c) Leu-Gly-Gly-Gly-Ser-Ala-Leu-Leu-Arg-Ser-Ile-Pro-Ala (SEQ ID NO:16);
  (d) Gly-Gly-Gly-Ser-Ala-Leu-Leu-Arg-Ser-Ile-Pro-Ala (SEQ ID NO:17);
  (e) Gly-Gly-Ser-Ala-Leu-Leu-Arg-Ser-Ile-Pro-Ala (SEQ ID NO:18); and
  (f) Gly-Ser-Ala-Leu-Leu-Arg-Ser-Ile-Pro-Ala (SEQ ID NO:19).

6. The method of claim 3, wherein the ADNF I polypeptide comprises up to 20 amino acids at the N-terminus or the C-terminus of the active core site.

7. The method of claim 1, wherein the ADNF polypeptide is an ADNF III polypeptide.

8. The method of claim 7, wherein the ADNF III polypeptide consists of the amino acid sequence Asn-Ala-Pro-Val-Ser-Ile-Pro-Gln (SEQ ID NO:2).

9. The method of claim 7, wherein the ADNF III polypeptide consists of an amino acid sequence selected from the group consisting of:
  (a) Gly-Gly-Asn-Ala-Pro-Val-Ser-Ile-Pro-Gln (SEQ ID NO:20);
  (b) Leu-Gly-Gly-Asn-Ala-Pro-Val-Ser-Ile-Pro-Gln-Gln-Ser (SEQ ID NO:21);
  (c) Leu-Gly-Leu-Gly-Gly-Asn-Ala-Pro-Val-Ser-Ile-Pro-Gln-Gln-Ser (SEQ ID NO:22); and
  (d) Ser-Val-Arg-Leu-Gly-Leu-Gly-Gly-Asn-Ala-Pro-Val-Ser-Ile-Pro-Gln-Gln-Ser (SEQ ID NO:23).

10. The method of claim 7, wherein the ADNF III polypeptide comprises up to 20 amino acids at the N-terminus or the C-terminus of the active core site.

11. The method of claim 1, wherein the ADNF polypeptide is a mixture of the ADNF I polypeptide of (a) and the ADNF III polypeptide of (b).

12. The method of claim 11, wherein the ADNF I polypeptide is consists of the amino acid sequence Ser-Ala-Leu-Leu-Arg-Ser-Ile-Pro-Ala (SEQ ID NO:1), and wherein the ADNF III polypeptide consists of the amino acid sequence Asn-Ala-Pro-Val-Ser-Ile-Pro-Gln (SEQ ID NO:2).

13. The method of claim 11, wherein the ADNF I polypeptide consists of an amino acid sequence selected from the group consisting of:
  (a) Val-Leu-Gly-Gly-Gly-Ser-Ala-Leu-Leu-Arg-Ser-Ile-Pro-Ala (SEQ ID NO:14);
  (b) Val-Glu-Glu-Gly-Ile-Val-Leu-Gly-Gly-Gly-Ser-Ala-Leu-Leu-Arg-Ser-Ile-Pro-Ala (SEQ ID NO:15);
  (c) Leu-Gly-Gly-Gly-Ser-Ala-Leu-Leu-Arg-Ser-Ile-Pro-Ala (SEQ ID NO:16);
  (d) Gly-Gly-Gly-Ser-Ala-Leu-Leu-Arg-Ser-Ile-Pro-Ala (SEQ ID NO:17);
  (e) Gly-Gly-Ser-Ala-Leu-Leu-Arg-Ser-Ile-Pro-Ala (SEQ ID NO:18);
  (f) Gly-Ser-Ala-Leu-Leu-Arg-Ser-Ile-Pro-Ala (SEQ ID NO:19); and
  (g) Ser-Ala-Leu-Leu-Arg-Ser-Ile-Pro-Ala (SEQ ID NO:1); and
  wherein the ADNF III polypeptide consists of an amino acid sequence selected from the group consisting of:
  (a) Asn-Ala-Pro-Val-Ser-Ile-Pro-Gln (SEQ ID NO:2);
  (b) Gly-Gly-Asn-Ala-Pro-Val-Ser-Ile-Pro-Gln (SEQ ID NO:20);
  (c) Leu-Gly-Gly-Asn-Ala-Pro-Val-Ser-Ile-Pro-Gln-Gln-Ser (SEQ ID NO:21);
  (d) Leu-Gly-Leu-Gly-Gly-Asn-Ala-Pro-Val-Ser-Ile-Pro-Gln-Gln-Ser (SEQ ID NO:22); and
  (e) Ser-Val-Arg-Leu-Gly-Leu-Gly-Gly-Asn-Ala-Pro-Val-Ser-Ile-Pro-Gln-Gln-Ser (SEQ ID NO:23).

14. The method of claim 11, wherein the ADNF I polypeptide comprises up to 20 amino acids at the N-terminus or the C-terminus of the active core site of the ADNF I polypeptide, and wherein the ADNF III polypeptide comprises up to 20 amino acids at the N-terminus or the C-terminus of the active core site of the ADNF III polypeptide.

15. The method of claim 1, wherein the condition is decreased body weight of the subject.

16. The method of claim 1, wherein the condition is decreased brain weight of the subject.

17. The method of claim 1, wherein the condition is a decreased level of VIP mRNA or protein of the subject.

18. The method of claim 1, wherein the condition is decreased viability of the subject in utero.

19. The method of claim 1, wherein the condition is decreased learning.

20. The method of claim 1, wherein step (ii) comprises administering the ADNF polypeptide directly to the subject.

21. The method of claim 1, wherein step (ii) comprises administering the ADNF polypeptide to the pregnant female during pregnancy.

* * * * *

```
                           SEQUENCE LISTING

<160> NUMBER OF SEQ ID NOS: 26

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence:activity
      dependent neurotrophic factor I (ADNF I) active
      site

<400> SEQUENCE: 1

Ser Ala Leu Leu Arg Ser Ile Pro Ala
 1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence:activity
      dependent neurotrophic factor III (ADNF III)
      active site

<400> SEQUENCE: 2

Asn Ala Pro Val Ser Ile Pro Gln
 1               5

<210> SEQ ID NO 3
<211> LENGTH: 89
<212> TYPE: PRT
<213> ORGANISM: Artificial Sequence
<220> FEATURE:
<223> OTHER INFORMATION: Description of Artificial Sequence:ADNF I
      polypeptide
<220> FEATURE:
<221> NAME/KEY: MOD_RES
<222> LOCATION: (1)..(40)
<223> OTHER INFORMATION: Xaa = any amino acid, Xaa at positions 1-40
      may be present or absent
<220> FEATURE:
<221> NAME/KEY: MOD_RES
```

```
<222> LOCATION: (50)..(89)
<223> OTHER INFORMATION: Xaa = any amino acid, Xaa at positions 50-89
      may be present or absent

<400> SEQUENCE: 3

Xaa Xaa Xaa Xaa Xaa Xaa Xaa Xaa Xaa Xaa Xaa Xaa Xaa Xaa Xaa Xaa
 1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Ser Ala Leu Leu Arg Ser Ile Pro
        35                  40                  45

Ala Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
 65                 70                  75                  80

Xaa Xaa Xaa Xaa Xaa Xaa Xaa Xaa Xaa
            85

<210> SEQ ID NO 4
<211> LENGTH: 88
<212> TYPE: PRT
<213> ORGANISM: Artificial Sequence
<220> FEATURE:
<223> OTHER INFORMATION: Description of Artificial Sequence:ADNF I
      polypeptide
<220> FEATURE:
<221> NAME/KEY: MOD_RES
<222> LOCATION: (1)..(40)
<223> OTHER INFORMATION: Xaa = any amino acid, Xaa at positions 1-40
      may be present or absent
<220> FEATURE:
<221> NAME/KEY: MOD_RES
<222> LOCATION: (49)..(88)
<223> OTHER INFORMATION: Xaa = any amino acid, Xaa at positions 49-88
      may be present or absent

<400> SEQUENCE: 4

Xaa Xaa Xaa Xaa Xaa Xaa Xaa Xaa Xaa Xaa Xaa Xaa Xaa Xaa Xaa Xaa
 1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Asn Ala Pro Val Ser Ile Pro Gln
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
 65                 70                  75                  80

Xaa Xaa Xaa Xaa Xaa Xaa Xaa Xaa
            85

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence:1-R or 2-R
      in ADNF I polypeptide formula

<400> SEQUENCE: 5

Val Leu Gly Gly Gly
 1               5

<210> SEQ ID NO 6
```

```
<211> LENGTH: 10
<212> TYPE: PRT
<213> ORGANISM: Artificial Sequence
<220> FEATURE:
<223> OTHER INFORMATION: Description of Artificial Sequence:1-R in ADNF
      I polypeptide formula

<400> SEQUENCE: 6

Val Glu Glu Gly Ile Val Leu Gly Gly Gly
 1               5                  10

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence:3-R or 4-R
      in ADNF III polypeptide formula

<400> SEQUENCE: 7

Leu Gly Leu Gly Gly
 1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence:3-R  in ADNF
      III polypeptide formula

<400> SEQUENCE: 8

Ser Val Arg Leu Gly Leu Gly Gly
 1               5

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence:2-R in ADNF
      I polypeptide formula

<400> SEQUENCE: 9

Val Leu Gly Gly
 1

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence:2-R in ADNF
      I polypeptide formula

<400> SEQUENCE: 10

Val Leu Gly Gly Val
 1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence:2-R in ADNF
      I polypeptide formula

<400> SEQUENCE: 11
```

-continued

```
Gly Val Leu Gly Gly
  1               5

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence:4-R in ADNF
      III polypeptide formula

<400> SEQUENCE: 12

Leu Gly Leu Gly
  1

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence:4-R in ADNF
      III polypeptide formula

<400> SEQUENCE: 13

Leu Gly Leu Gly Leu
  1               5

<210> SEQ ID NO 14
<211> LENGTH: 19
<212> TYPE: PRT
<213> ORGANISM: Artificial Sequence
<220> FEATURE:
<223> OTHER INFORMATION: Description of Artificial Sequence:ADNF I
      polypeptide

<400> SEQUENCE: 14

Val Leu Gly Gly Gly Ser Ala Leu Leu Arg Ser Ile Pro Ala Val Leu
  1               5                  10                  15

Gly Gly Gly

<210> SEQ ID NO 15
<211> LENGTH: 18
<212> TYPE: PRT
<213> ORGANISM: Artificial Sequence
<220> FEATURE:
<223> OTHER INFORMATION: Description of Artificial Sequence:ADNF I
      polypeptide

<400> SEQUENCE: 15

Val Leu Gly Gly Gly Ser Ala Leu Leu Arg Ser Ile Pro Ala Val Leu
  1               5                  10                  15

Gly Gly

<210> SEQ ID NO 16
<211> LENGTH: 19
<212> TYPE: PRT
<213> ORGANISM: Artificial Sequence
<220> FEATURE:
<223> OTHER INFORMATION: Description of Artificial Sequence:ADNF I
      polypeptide

<400> SEQUENCE: 16

Val Leu Gly Gly Gly Ser Ala Leu Leu Arg Ser Ile Pro Ala Val Leu
  1               5                  10                  15

Gly Gly Val
```

<210> SEQ ID NO 17
<211> LENGTH: 19
<212> TYPE: PRT
<213> ORGANISM: Artificial Sequence
<220> FEATURE:
<223> OTHER INFORMATION: Description of Artificial Sequence:ADNF I
      polypeptide

<400> SEQUENCE: 17

Val Leu Gly Gly Gly Ser Ala Leu Leu Arg Ser Ile Pro Ala Gly Val
 1               5                  10                  15

Leu Gly Gly

<210> SEQ ID NO 18
<211> LENGTH: 18
<212> TYPE: PRT
<213> ORGANISM: Artificial Sequence
<220> FEATURE:
<223> OTHER INFORMATION: Description of Artificial Sequence:ADNF III
      polypeptide

<400> SEQUENCE: 18

Leu Gly Leu Gly Gly Asn Ala Pro Val Ser Ile Pro Gln Leu Gly Leu
 1               5                  10                  15

Gly Gly

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence:ADNF III
      polypeptide

<400> SEQUENCE: 19

Leu Gly Leu Gly Gly Asn Ala Pro Val Ser Ile Pro Gln Leu Gly Leu
 1               5                  10                  15

Gly

<210> SEQ ID NO 20
<211> LENGTH: 18
<212> TYPE: PRT
<213> ORGANISM: Artificial Sequence
<220> FEATURE:
<223> OTHER INFORMATION: Description of Artificial Sequence:ADNF III
      polypeptide

<400> SEQUENCE: 20

Leu Gly Leu Gly Gly Asn Ala Pro Val Ser Ile Pro Gln Leu Gly Leu
 1               5                  10                  15

Gly Leu

<210> SEQ ID NO 21
<211> LENGTH: 14
<212> TYPE: PRT
<213> ORGANISM: Artificial Sequence
<220> FEATURE:
<223> OTHER INFORMATION: Description of Artificial Sequence:ADNF I
      polypeptide

<400> SEQUENCE: 21

Val Leu Gly Gly Gly Ser Ala Leu Leu Arg Ser Ile Pro Ala
 1               5                  10

```
<210> SEQ ID NO 22
<211> LENGTH: 19
<212> TYPE: PRT
<213> ORGANISM: Artificial Sequence
<220> FEATURE:
<223> OTHER INFORMATION: Description of Artificial Sequence:ADNF I
      polypeptide

<400> SEQUENCE: 22

Val Glu Glu Gly Ile Val Leu Gly Gly Gly Ser Ala Leu Leu Arg Ser
 1               5                  10                  15

Ile Pro Ala

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence:ADNF III
      polypeptide

<400> SEQUENCE: 23

Gly Gly Asn Ala Pro Val Ser Ile Pro Gln
 1               5                  10

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence:ADNF III
      polypeptide

<400> SEQUENCE: 24

Leu Gly Gly Asn Ala Pro Val Ser Ile Pro Gln Gln Ser
 1               5                  10

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence:ADNF III
      polypeptide

<400> SEQUENCE: 25

Leu Gly Leu Gly Gly Asn Ala Pro Val Ser Ile Pro Gln Gln Ser
 1               5                  10                  15

<210> SEQ ID NO 26
<211> LENGTH: 18
<212> TYPE: PRT
<213> ORGANISM: Artificial Sequence
<220> FEATURE:
<223> OTHER INFORMATION: Description of Artificial Sequence:ADNF III
      polypeptide

<400> SEQUENCE: 26

Ser Val Arg Leu Gly Leu Gly Gly Asn Ala Pro Val Ser Ile Pro Gln
 1               5                  10                  15

Gln Ser
```